United States Patent
Kim et al.

(10) Patent No.: US 10,272,437 B2
(45) Date of Patent: Apr. 30, 2019

(54) PCR HEATING BLOCK HAVING PATTERN HEATER REPEATEDLY ARRANGED THEREON AND PCR DEVICE HAVING THE SAME

(71) Applicant: NANOBIOSYS INC., Seoul (KR)

(72) Inventors: Sung-Woo Kim, Seoul (KR);
Jung-Hwan Lee, Anyang-si (KR);
Duck-Joong Kim, Anyang-si (KR)

(73) Assignee: NANOBIOSYS INC., Seoul (KR)

( * ) Notice: Subject to any disclaimer, the term of this patent is extended or adjusted under 35 U.S.C. 154(b) by 316 days.

(21) Appl. No.: 14/777,540

(22) PCT Filed: Mar. 18, 2014

(86) PCT No.: PCT/KR2014/002284
§ 371 (c)(1),
(2) Date: Sep. 16, 2015

(87) PCT Pub. No.: WO2014/148800
PCT Pub. Date: Sep. 25, 2014

(65) Prior Publication Data
US 2016/0279639 A1    Sep. 29, 2016

(30) Foreign Application Priority Data
Mar. 18, 2013  (KR) .......................... 10-2013-0028772

(51) Int. Cl.
*B01L 7/00* (2006.01)
*G01N 21/64* (2006.01)
(Continued)

(52) U.S. Cl.
CPC .......... *B01L 7/525* (2013.01); *G01N 21/6486* (2013.01); *G01N 27/3277* (2013.01);
(Continued)

(58) Field of Classification Search
CPC .. B01L 7/525; B01L 2200/14; B01L 2200/10; B01L 2200/12; B01L 2300/0645;
(Continued)

(56) References Cited

U.S. PATENT DOCUMENTS

2005/0032198 A1    2/2005   Wittwer et al.
2005/0139993 A1*   6/2005   Lee .................. B01J 9/0093
                                                257/706

(Continued)

FOREIGN PATENT DOCUMENTS

JP    2004-305009 A    11/2004
JP    2005-323519 A    11/2005
(Continued)

OTHER PUBLICATIONS

J Kang et al., "Simulation and Optimization of a Flow-Through Micro PCR Chip", NSTI-Nanotech, vol. 2, Jun. 11, 2007, pp. 585-588.
(Continued)

*Primary Examiner* — Michael L Hobbs
(74) *Attorney, Agent, or Firm* — Novick, Kim & Lee, PLLC; Sang Ho Lee

(57) ABSTRACT

Provided is a PCR heating block having heaters repeatedly arranged thereon is capable of preventing the radial thermal distribution generated from the individual heaters and the non-uniform heat superposition between the adjacent heaters improve the PCR yield and further capable of requiring no separate temperature controlling mechanism to achieve the miniaturization and integration of a device. Furthermore, a PCR device is capable of amplifying a plurality of nucleic acid samples at the same time and rapidly by using a PCR heating block on which heater units are repeatedly arranged and a plate-shaped PCR reaction unit and also capable of measuring successively generated optical signals electro-
(Continued)

chemical signals to in real time check the nucleic acid amplification.

19 Claims, 24 Drawing Sheets

(51) Int. Cl.
    *G01N 27/327*     (2006.01)
    *B01L 3/00*     (2006.01)

(52) U.S. Cl.
    CPC ......... *B01L 3/5027* (2013.01); *B01L 2200/10* (2013.01); *B01L 2200/12* (2013.01); *B01L 2200/14* (2013.01); *B01L 2300/0627* (2013.01); *B01L 2300/0645* (2013.01); *B01L 2300/087* (2013.01); *B01L 2300/0816* (2013.01); *B01L 2300/12* (2013.01); *B01L 2300/1827* (2013.01); *B01L 2400/0487* (2013.01)

(58) Field of Classification Search
    CPC ......... B01L 2300/12; B01L 2300/0627; B01L 2300/1827; B01L 2300/087; B01L 2300/0816; B01L 2400/0487; B01L 3/5027; G01N 21/6486; G01N 27/3277
See application file for complete search history.

(56) References Cited

U.S. PATENT DOCUMENTS

| 2007/0242105 | A1 | 10/2007 | Srinivasan et al. |
| 2008/0131956 | A1 | 6/2008 | Chung et al. |
| 2009/0186404 | A1* | 7/2009 | Kim ..................... B01L 3/5027 435/303.1 |

FOREIGN PATENT DOCUMENTS

| JP | 2006-523095 A | 10/2006 |
| KR | 10-2005-0003944 A | 1/2005 |
| KR | 10-2012-0137054 A | 12/2012 |
| KR | 10-2012-0139205 A | 12/2012 |
| KR | 10-2012-0139206 A | 12/2012 |
| RU | 2177830 C2 | 1/2002 |
| WO | 2013-027393 A1 | 2/2013 |

OTHER PUBLICATIONS

Bertrand Selva et al., "Integration of a uniform and rapid heating source into microfluidic systems", Microfluid Nanofluid, Oct. 14, 2009, pp. 755-765.

* cited by examiner

111

PCR HEATING BLOCK HAVING PATTERN HEATER REPEATEDLY ARRANGED THEREON AND PCR DEVICE HAVING THE SAME

TECHNICAL FIELD

The present invention relates to a PCR device that is provided with a PCR heating block having heaters continuously and repeatedly arranged thereon.

BACKGROUND ART

PCR (polymerase chain reaction) is a technology that a specific region of template DNA is repeatedly heated and cooled, the specific region is successively replicated, and the DNA having the specific region is amplified exponentially. The PCR is widely used for the purposes of analysis and diagnosis in various fields like biotechnology, genetic engineering, medicine and so on. Recently, a variety of devices for efficiently conducting the PCR have been developed.

According to a conventional PCR device, a container in which a sample solution having template DNA is accommodated is mounted on a single heater, and the container is repeatedly heated and cooled, thus conducting PCR. Since the PCR device has one heater, in this case, it is not complicated in structure, but it has to have a complicated circuit for controlling accurate temperatures. Further, the heating and the cooling need to be repeatedly carried out with one single heater which resulting in unpreferably extending the total time consumed for the PCR.

According to another conventional PCR device, further, a plurality of heaters having PCR temperatures are mounted, and a sample solution having template DNA flows along one channel passing through the heaters, thus conducting PCR. Since the PCR device has the plurality of heaters, the PCR device has a relatively simple circuit, but has to have a long channel passing through high temperature heaters and lower temperature heaters. Thus, the PCR device has complicated structure. Further, an additional controller is required to control the flow rate of the sample solution which includes the DNA and flows along the channel passing through the heaters.

On the other hand, recently, there have been proposed PCR devices capable of increasing PCR yield, recognizing PCR process in real time, and further achieving miniaturization and portability through miniaturized heaters. Since the performance of the miniaturized heaters gives a big influence on the PCR yield, in this case, it is very important to accurately control given temperatures of the miniaturized heaters. Accordingly, there is a definite need to develop a new PCR device capable of drastically reducing PCR time, providing reliable PCR yield, and achieving miniaturization and portability thereof.

DISCLOSURE

Technical Problem

Accordingly, the present invention is provided to overcome the above-mentioned problems found in the prior art. The present invention is proposed to provide a PCR heating block reducing PCR time, increasing PCR yield, and achieving miniaturization and portability of a product, and to provide a PCR device having the same.

Technical Solution

According to the first embodiment of the present invention, a PCR heating block is provided, which includes two or more heaters repeatedly arranged thereon. Each heater has a compensated pattern adapted to adjust a resistance on at least a portion thereof, to control heating uniformity on the surface thereof, and to prevent the occurrence of non-uniform heat superposition between the adjacent heaters due to radial heat distribution generated from each heater.

According to the first embodiment of the present invention, the compensated pattern has spaces repeatedly formed on at least a portion of each heater to adjust a resistance on each heater and thus to control the heat uniformity on the surface of each heater.

The compensated pattern has the spaces formed on at least a portion of each heater in such a manner as to have different line widths from each other to adjust the resistance on each heater and thus control the heat uniformity on the surface of each heater.

The compensated pattern has at least a portion of each heater in such a manner as to have a different thickness to adjust the resistance on each heater and thus control the heat uniformity on the surface of each heater.

The compensated pattern has at least a portion of each heater in such a manner as to have a different material to adjust the resistance on each heater and thus control the heat uniformity on the surface of each heater.

The compensated pattern has at least a portion of each heater in such a manner as to have a different arrangement to adjust the resistance on each heater and thus control the heat uniformity on the surface of each heater.

According to a second embodiment of the present invention, a PCR chip is provided, which includes a PCR heating block according to the first embodiment of the present invention, and a plate-shaped PCR reaction unit bonded to the PCR heating block in such a manner as to conduct heat exchanging with the PCR heating block and having one or more reaction channels extended to pass through the portions corresponding to the upper sides of the heaters arranged on the PCR heating block in a longitudinal direction thereof, each reaction channel having an inlet and an outlet formed on both ends thereof.

According to the second embodiment of the present invention, an insulator is formed on a top surface of the PCR heating block to prevent an occurrence of electrolysis of a PCR solution.

According to a third embodiment of the present invention, a PCR device is provided which includes a PCR heating block according to the first embodiment of the present invention, a plate-shaped PCR reaction unit bonded to the PCR heating block in such a manner as to conduct heat exchanging with the PCR heating block and having one or more reaction channels extended to pass through the portions corresponding to an upper sides of the heaters arranged on the PCR heating block in a longitudinal direction thereof, each reaction channel having an inlet and an outlet formed on both ends thereof, and a power supply part supplying power to the heaters repeatedly arranged on the PCR heating block.

According to the third embodiment of the present invention, a heater protection insulator is formed on a top surface of the PCR heating block.

The PCR device further includes pumps adapted to provide positive pressure or negative pressure so as to control the flow rate of the PCR solution flowing in the reaction channels.

The PCR device further includes light sources adapted to provide light to the PCR reaction unit and light detectors adapted to detect the light emitted from the light sources.

The light sources and the light detectors are repeatedly arranged in the spaces between the adjacent heaters of the PCR heating block.

The PCR reaction unit includes detection electrodes spaced apart from each other in such a manner as to traverse the undersides of the reaction channels in a longitudinal direction of the reaction channels so as to detect electrochemical signals generated from a bonding of amplified nucleic acid to a redox indicator in the reaction channels, and the detection electrodes located between two or more heater groups when coming into thermal contact with the PCR heating block.

The PCR device further includes an electrochemical signal measuring module electrically connected to the detection electrodes to measure the electrochemical signals generated from the interiors of the reaction channels of the PCR reaction unit in real time.

The PCR reaction unit includes immobilization layers repeatedly spaced apart from each other on one region of the reaction channels in such a manner as to traverse the sections of the reaction channels in a longitudinal direction of the reaction channels and subjected to surface treatment with capture probes complementarily bonded to one region of amplified target nucleic acid and detection electrodes formed on the other region of the reaction channels so as to detect electrochemical signals, and the reaction channels contain composites having metal nanoparticles and signaling probes connected to the metal nanoparticles in such a manner as to be complementarily bonded to the other region of the amplified target nucleic acid.

The PCR device further includes an electrochemical signal measuring module electrically connected to the detection electrodes to measure the electrochemical signals generated from the interiors of the reaction channels of the PCR reaction unit in real time.

Advantageous Effects

According to one embodiment of the present invention, the PCR heating block having the heaters repeatedly arranged thereon is capable of preventing the radial thermal distribution generated from the individual heaters and the non-uniform heat superposition between the adjacent heaters to improve PCR yield and further capable of requiring no separate temperature controlling means to achieve the miniaturization and integration of the device. Furthermore, the PCR device is capable of amplifying a plurality of nucleic acid samples at the same time and rapidly by using the PCR heating block on which the heater units are repeatedly arranged and the plate-shaped PCR reaction unit and also capable of measuring successively generated optical signals or electrochemical signals to check the process of nucleic acid amplification in real time.

DETAILED DESCRIPTION

Hereinafter, embodiments according to the present invention will be described in detail with reference to the attached figures. Explanation below is merely exemplary of the embodiments according to the present invention for easier understanding and it does not be meant to limit the protection scope thereto.

According to the embodiment of the present invention, PCR (Polymerase Chain Reaction) refers to a type of reaction for amplifying nucleic acids having specific sequence. So as to amplifying DNA (deoxyribonucleic acid) having specific sequence, for example, a PCR device conducts a denaturing step that a solution containing a PCR sample in which double-stranded DNA as template nucleic acid is contained and a reagent is heated to a given temperature, for example, about 95° C. and the double-stranded DNA is separated to single-stranded DNA, an annealing step that an oligonucleotide primer having a complementary sequence to the sequence of the DNA to be amplified is provided and cooled to a given temperature, for example, 55° C., together with the separated single-stranded DNA, and the primer is then bonded to the specific sequence of the single-stranded DNA to form a partial DNA-primer composite, and an extension (amplification) step that the solution is maintained to an appropriate temperature, for example, 72° C. after the annealing step and double-stranded DNA is formed on the basis of the primer of the partial DNA-primer composite by means of DNA polymerase. In this case, the three steps are repeatedly conducted 20 to 40 times to allow the DNA having the specific sequence to be amplified exponentially. In some cases, the PCR device conducts the annealing step and the extension (or amplification) step, at the same time, and at this time, the PCR device conducts two steps including the denaturing step and the annealing and extension step, thus finishing a first cycle. Accordingly, a PCR heating block and a PCR device having the same according to the embodiment of the present invention includes modules with which the above-mentioned steps are conducted. It is assumed that detailed modules not described herein have been disclosed in conventional technologies for the PCR or provided herein within the obvious scope of the present invention.

Figure 1:
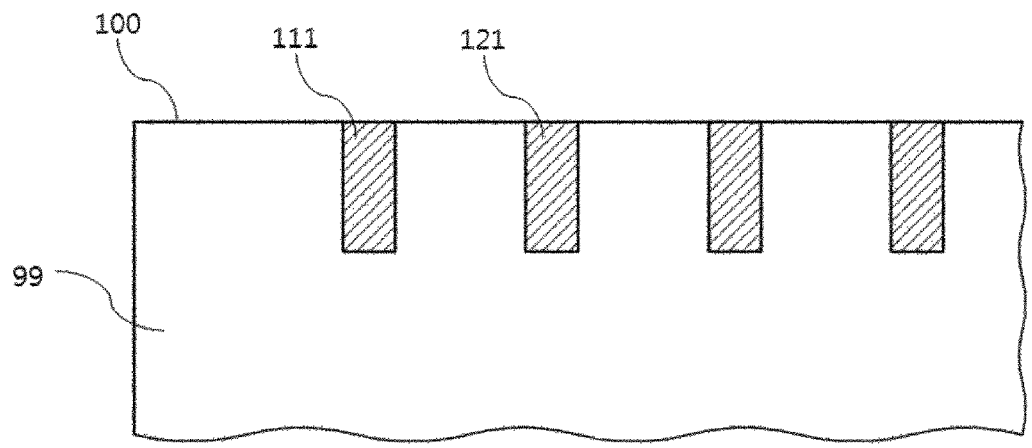
FIG. 1 depicts a PCR heating block 100 on which at least two heaters 111 and 121 are repeatedly arranged.

FIG. 1 depicts a PCR heating block 100 on which at least two heaters 111 and 121 are repeatedly arranged. FIGS. 2 to 6 depicts heater arrangements constituting the PCR heating block 100 according to the embodiment of the present invention.

Referring to FIG. 1, a PCR heating block 100 supplying heat to a PCR solution, on which two or more heaters 111 and 121 are repeatedly arranged, is provided. The PCR heating block 100 is a module for supplying given heat to the PCR solution, that is, a sample and reagent for conducting PCR and includes a contacted surface with a PCR reaction unit having the sample and reagent accommodated into at least one surface thereof, so that heat is supplied to the PCR solution through the thermal contact with one surface of the PCR reaction unit, thus conducting the PCR.

Referring to FIGS. 2 to 6, a substrate 99 is disposed under the PCR heating block 100. Substrate 99 does not change in physical or chemical properties due to the heating of the heaters 111 and 121 arranged on the surface thereof and made of a material causing no frequent exchange of heat between the two or more heaters 111 and 121. For example, substrate 99 is made of a material like plastic, glass and silicone, and if necessary, it may be transparent or translucent. To achieve miniaturization and integration of a device, the PCR heating block 100 is formed of a generally thin plate having a thickness in the range of about 50 nm to 1 mm, and preferably, a thickness of about 250 µm. However, the thickness of the PCR heating block 100 is not limited thereto. The two or more heaters are repeatedly arranged on the PCR heating block 100, and for example, the PCR heating block 100 includes two or more heater groups, each having one or more heaters. In this case, two or more heater units, each having the two or more heater groups, are spaced apart from each other on the PCR heating block 100. Further, the contacted surface of the PCR heating block 100 with the PCR reaction unit 900 has various shapes like a plane, channel, or pillar capable of increasing the surface to volume ratio, so that the heat can be efficiently supplied to the PCR reaction unit 900 into which the PCR solution is accommodated.

The heaters 111, 112, 121, 122, 131 and 132 are conductive heating elements arranged or printed on the substrate 99 and may be formed of heaters using Joule heating or thermoelements causing the Peltier effect. The heaters 111, 112, 121, 122, 131 and 132 are operably connected to various power modules and control modules in order to maintain given temperatures and are also operably connected to sensors monitoring the temperatures of the heaters. So as to allow the internal temperatures of the heaters 111, 112, 121, 122, 131 and 132 to be constantly maintained, unit electrodes, that is, heater electrodes are symmetrically arranged in up and down and/or left and right directions around the center points of the surfaces of the heaters. So as to achieve rapid heat transmission and high conductivity, further, the heaters 111, 112, 121, 122, 131 and 132 are made of one or more materials selected from the group consisting of chrome, aluminum, copper, iron, silver and carbon, or made of their composite materials. However, the materials of the heaters are not limited thereto. Furthermore, the heaters 111, 112, 121, 122, 131 and 132 may include one or more materials selected from the group consisting of conductive nanoparticles containing light transmission heating elements, for example, an oxide semiconductor and a material to which impurities selected from the group consisting of In, Sb, Al, Ga, C and Sn are added to the oxide semiconductor, indium tin oxide, conductive polymer, carbon nanotube and graphene.

The heater groups 110, 120 and 130 includes one or more heaters 111, 112, 121, 122, 131 and 132 therein and refer to portions on which given temperatures are maintained to conduct the denaturing step, the annealing step and/or the extension step for the PCR. The two or more heater groups 110, 120 and 130 are arranged on the PCR heating block 100, and they are spaced apart from each other on the substrate 99. Preferably, the two to four heater groups can be arranged on the PCR heating block 100. If two heater groups are arranged on the PCR heating block 100, the first heater group maintains the temperature of the PCR denaturing step, and the second heater group maintains the temperature of the PCR annealing/extension step. Otherwise, the first heater group maintains the temperature of the PCR annealing/extension step, and the second heater group maintains the temperature of the PCR denaturing step. On the other hand, if three heater groups are arranged on the PCR heating block 100, the first heater group maintains the temperature of the PCR denaturing step, the second heater group maintains the temperature of the PCR annealing step, and the third heater group maintains the temperature of the PCR extension step. Otherwise, the first heater group maintains the temperature of the PCR annealing step, the second heater group maintains the temperature of the PCR extension step, and the third heater group maintains the temperature of the PCR denaturing step. Otherwise, the first heater group maintains the temperature of the PCR extension step, the second heater group maintains the temperature of the PCR denaturing step, and the third heater group maintains the temperature of the PCR annealing step. Preferably, the three heater groups can be arranged on the PCR heating block 100 to maintain the respective temperatures of the three steps for the PCR, that is, the denaturing step, the annealing step and the extension step. More preferably, the two heater groups can be arranged on the PCR heating block 100 to maintain the respective temperatures of the two steps for the PCR, that is, the denaturing step and the annealing/extension step. In the case that the two heater groups are arranged on the PCR heating block 100 to maintain the respective temperatures of the two steps for the PCR, that is, the denaturing step and the annealing/extension step, the PCR time is shorter than that required for the three steps including the denaturing step, the annealing step and the extension step. Furthermore, since the number of heaters is reduced, it has advantages enhancing the simplification and integrity of the structure. In the three steps for PCR, on the other hand, the temperature of the denaturing step is in the range of 85 to 105° C., preferably 95° C., the temperature of the annealing step is in the range of 40 to 60° C., preferably 50° C., and the temperature of the extension step is in the range of 50 to 80° C., preferably 72° C. In the two steps for PCR, furthermore, the temperature of the denaturing step is in the range of 85 to 105° C., preferably 95° C., and the temperature of the annealing/extension step is in the range of 50 to 80° C., preferably 72° C. However, the given temperatures and the ranges of the given temperatures for the PCR may be of course adjustable in the range known. The heater groups 110, 120 and 130 further include another heaters serving to buffer the temperatures.

Heater units 10 and 20 are units including the two or more heater groups with each having one or more heaters and mean regions on which a first cycle having the denaturing step, the annealing step and/or the extension step for the PCR is finished. The heater units 10 and 20 are arranged repeatedly two or more times on the PCR heating block 100, and preferably, the heater units 10 and 20 are arranged repeatedly 10 times, 20 times, 30 times or 40 times on the PCR heating block 100.

Figure 2:
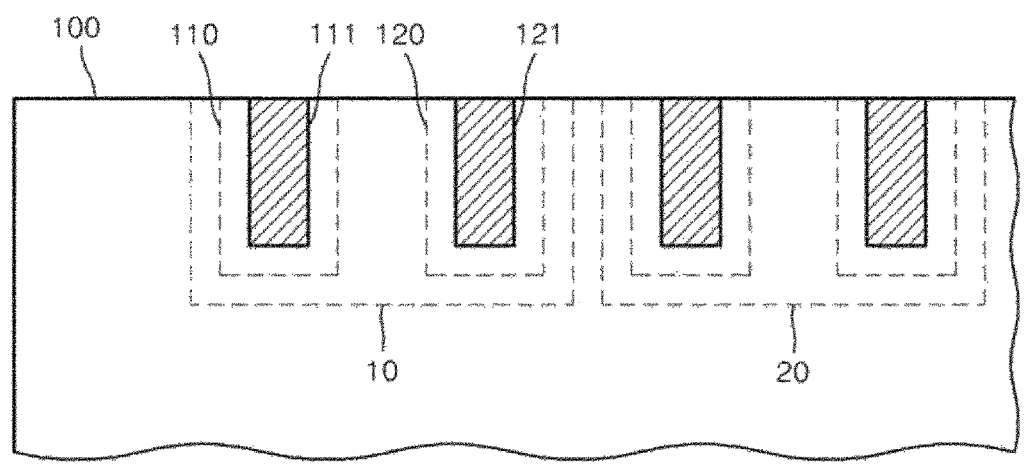
FIGS. 2 to 6 depicts heater arrangements constituting the PCR heating block 100 according to the embodiment of the present invention.

Referring to FIG. 2, the PCR heating block 100 includes the heater units 10 and 20 repeatedly arranged on the upper surface thereof, the two heater groups 110 and 120 disposed in each heater unit, and the heaters 111 and 121 disposed in the respective heater groups, and thus provides the temperatures of the two steps for PCR, that is, sequentially and repeatedly provides the first temperature of the denaturing step and the first temperature of the annealing/extension step. For example, the first heater 111 maintains the first temperature in the range of 85 to 105° C., preferably 95° C., so that the first heater group 110 provides the temperature of the denaturing step, and the second heater 121 maintains the temperature in the range of 50 to 80° C., preferably 72° C., so that the second heater group 120 provides the temperature of the annealing/extension step. Accordingly, the PCR heating block 100 sequentially and repeatedly provides the temperatures of the two steps for the PCR from the first heater unit 10 and the second heater unit 20.

Figure 3:
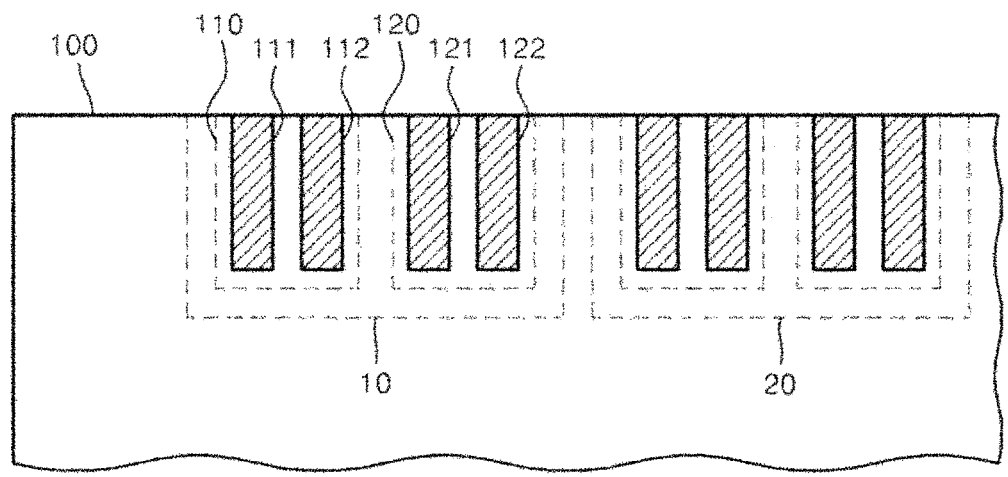

Referring to FIG. 3, the PCR heating block 100 includes the heater units 10 and 20 repeatedly arranged on the upper surface thereof, the two heater groups 110 and 120 disposed in each heater unit, and the two heaters 111 and 112, or 121 and 122 disposed in the respective heater groups, and thus provides the temperatures of the two steps for PCR, that is, sequentially and repeatedly provides the second temperature of the denaturing step and the second temperature of the annealing/extension step. For example, the first placed heater 111 maintains the first temperature in the range of 85 to 105° C., and the second placed heater 112 maintains the first temperature that is the same as or different from the temperature of the first heater 111 in the range of 85 to 105° C., so that the first heater group 110 provides the temperature of the denaturing step. The third placed heater 121 maintains the first temperature in the range of 50 to 80° C., and the fourth placed heater 122 maintains the first temperature that is the same as or different from the temperature of the third placed heater 121 in the range of 50 to 80° C., so that the second heater group 120 provides the temperature of the annealing/extension step. Accordingly, the PCR heating block 100 sequentially and repeatedly provides the temperatures of the two steps for the PCR from the first heater unit 10 and the second heater unit 20.

Figure 4:
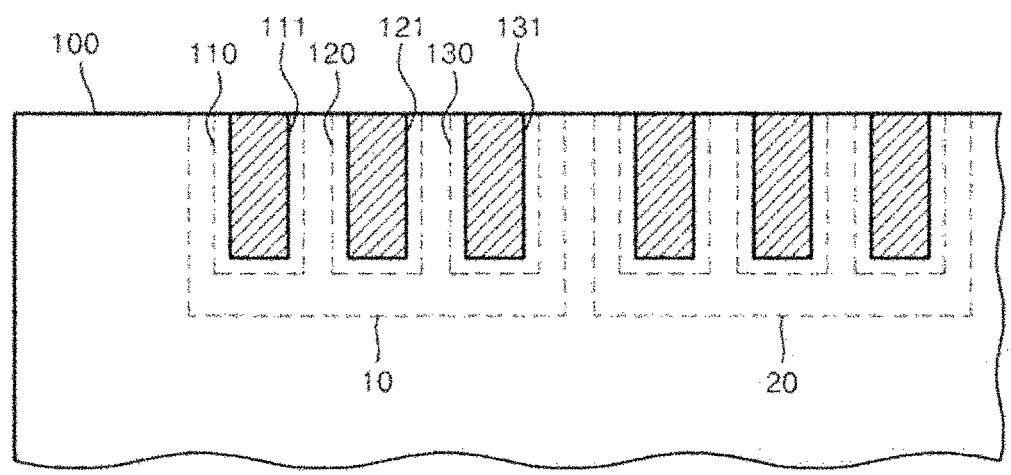

Referring to FIG. 4, the PCR heating block 100 includes the heater units 10 and 20 repeatedly arranged on the upper surface thereof, the three heater groups 110, 120 and 130 disposed in each heater unit, and the heaters 111, 121 and 131 disposed in the respective heater groups, and thus provides the temperatures of the three steps for PCR, that is, sequentially and repeatedly provides the first temperature of the denaturing step, the first temperature of the annealing step, and the first temperature of the extension step. For example, the first heater 111 maintains the first temperature in the range of 85 to 105° C., preferably 95° C., so that the first heater group 110 provides the temperature of the denaturing step, and the second heater 121 maintains the first temperature in the range of 40 to 60° C., preferably 50° C., so that the second heater group 120 provides the temperature of the annealing step. Further, the third heater 131 maintains the first temperature in the range of 50 to 80° C., preferably 72° C., so that the third heater group 130 provides the temperature of the extension step. Accordingly, the PCR heating block 100 sequentially and repeatedly provides the temperatures of the three steps for the PCR from the first heater unit 10 and the second heater unit 20.

Figure 5:
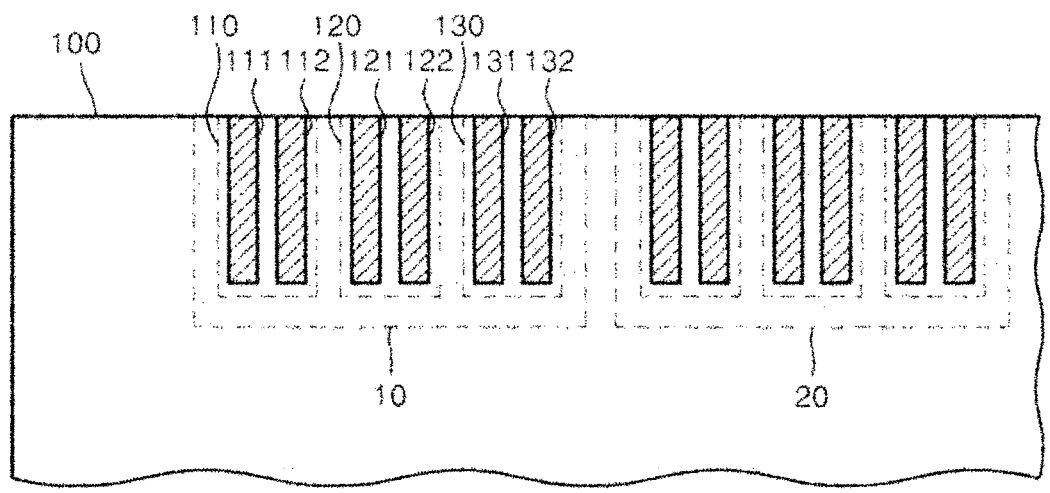

Referring to FIG. 5, the PCR heating block 100 includes the heater units 10 and 20 repeatedly arranged on an upper surface thereof, the three heater groups 110, 120 and 130 disposed in each heater unit, and the two heaters 111 and 121, 121 and 122, or 131 and 132 disposed in the respective heater groups, and thus provides the temperatures of the three steps for PCR, that is, sequentially and repeatedly provides the second temperature of the denaturing step, the second temperature of the annealing step and the second temperature of the extension step. For example, the first placed heater 111 maintains the first temperature in the range of 85 to 105° C., and the second placed heater 112 maintains the first temperature that is the same as or different from the temperature of the first heater 111 in the range of 85 to 105° C., so that the first heater group 110 provides the temperature of the denaturing step. The three placed heater 121 maintains the first temperature in the range of 40 to 60° C., and the fourth placed heater 122 maintains the first temperature that is the same as or different from the temperature of the three placed heater 121 in the range of 40 to 60° C., so that the second heater group 120 provides the temperature of the annealing step. The fifth heater 131 maintains the first temperature in the range of 50 to 80° C., and the sixth heater 132 maintains the first temperature that is the same as or different from the temperature of the fifth heater 131 in the range of 50 to 80° C., so that the third heater group 130 provides the temperature of the extension step. Accordingly, the PCR heating block 100 sequentially and repeatedly provides the temperatures of the three steps for the PCR from the first heater unit 10 and the second heater unit 20.

Referring to FIGS. 2 to 5, the two or more heaters 111, 112, 121, 122, 131 and 132 maintaining the given temperatures are repeatedly arranged on the PCR heating block 100, thus substantially increasing the temperature to time ratio. According to the conventional device where a single heater is disposed, for example, the temperature to time ratio is in the range of 3 to 7° C. per second. However, according to the embodiment of the present invention having repeatedly arranged heater structure, the temperature to time ratio between the heaters is in the range of 20 to 40° C. per second, thus reducing the time for PCR. According to the embodiment of the present invention having repeatedly arranged heater structure, the temperatures at the denaturing step, the annealing step and the extension step (or the denaturing step and the annealing/extension step) can be accurately controlled, and further, it is possible to maintain desired temperatures or temperature ranges only at portions at which heat is supplied from the heaters. Also, a various number of the heater units 10 and 20 are repeatedly arranged on the PCR heating block 100, thus achieving various PCR cycle times. For example, in case of the PCR having 10 cycles, the heater units are repeatedly arranged 10 times. That is, the heater units may be repeatedly arranged e.g., 10 times, 20 times, 30 times, 40 times, or 50 times on the PCR heating block 100 according to intended PCR cycles. Moreover, the heater units may be repeatedly arranged having the half of the number of the PCR cycles. For example, in case of the PCR having 20 cycles, the heater units may be repeatedly arranged 10 times. In this case, the sample and reagent solution flows 10 times in a direction from an inlet to an outlet through a reaction channel of a PCR reaction unit as described later. In continuation of that, it is also possible to arrange that the solution flows 10 times in a direction from the outlet to the inlet on the reaction channel of the PCR reaction unit.

Figure 6:
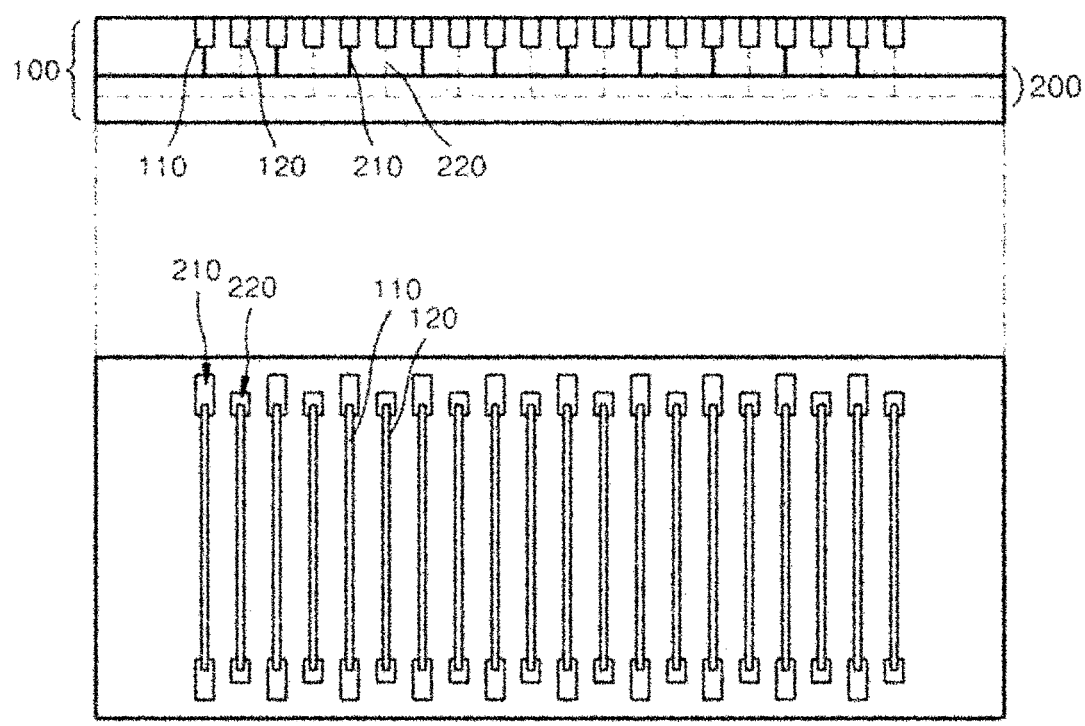

FIG. 6 shows the PCR heating block 100 according to the present invention and a power supply part 200 supplying power to the heaters repeatedly arranged on the PCR heating block 100. In more detail, the upper end portion of FIG. 6 shows a vertical sectional view of the PCR heating block 100, and the lower end portion of FIG. 6 shows a plan view of the PCR heating block 100. Referring to FIG. 6, the PCR heating block 100 includes the heater units repeatedly arranged 10 times, and each heater unit includes first and second heater groups each having one heater, that is, the first heater 110 and the second heater 120. The power supply part 200 is a module supplying power to the PCR heating block 100 from a power supply source so as to heat the PCR heating block 100 and includes first and second distributed wires 210 and 220 adapted to distribute power to the heaters 110 and 120.

Referring to FIG. 6, for example, the first distributed wire 210 of the PCR heating block 100 is located to supply power to the first heaters 110, and the second distributed wire 220 of the PCR heating block 100 is located to supply power to the second heaters 120. If the first heaters 110 maintain a temperature of the PCR denaturing step, for example, a temperature of 85 to 105° C. and the second heaters 120 maintains a temperature of the PCR annealing/extension step, for example, a temperature of 50 to 80° C., the first distributed wire 210 receives the power for maintaining the temperature of the PCR denaturing step from the power supply part 200 and the second distributed wire 220 receives the power for maintaining the temperature of the PCR annealing/extension step from the power supply part 200. The first distributed wire 210 and the second distributed wire 220 are made of a conductive material like gold, silver, copper and so on, but they are not limited thereto.

Figure 7:
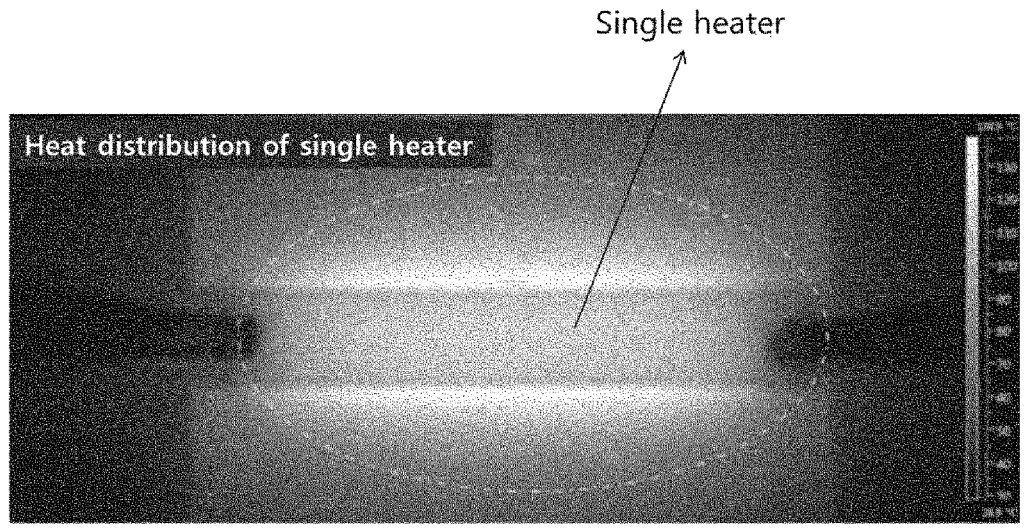
FIG. 7 is a photograph showing a non-uniform radial heat distribution generated from an individual heater when power is supplied to the individual heater on which no compensated pattern is formed.
Figure 8:
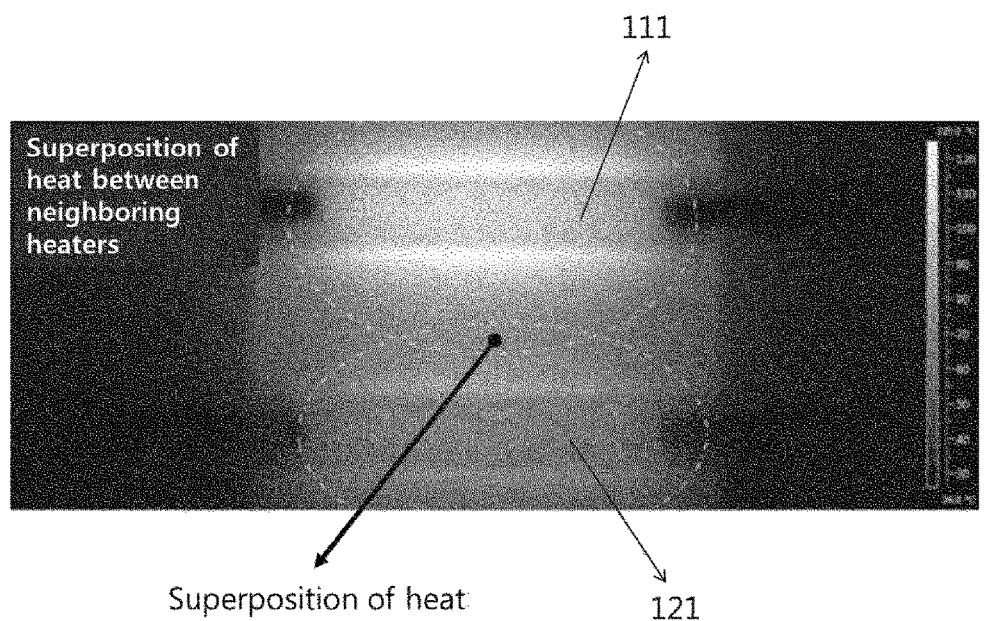
FIG. 8 is a photograph showing a non-uniform heat superposition between adjacent heaters 111 and 121 according to the non-uniform radial heat distribution generated from an individual heater when power is supplied to the at least two heaters in a state that the at least two heaters on which no compensated pattern is formed are repeatedly arranged on the PCR heating block.

FIG. 7 is a photograph showing a non-uniform radial heat distribution generated from an individual heater when power is supplied to the individual heater on which no compensated pattern is formed. FIG. 8 is a photograph showing a non-uniform heat superposition between adjacent heaters 111 and 121 according to the non-uniform radial heat distribution generated from an individual heater when power is supplied to the at least two heaters in a state that the at least two heaters on which no compensated pattern is formed are repeatedly arranged on the PCR heating block.

Referring to FIG. 7, radial heat distribution is formed from a single heater having a generally rectangular edge when the heater is heated by the power supplied thereto. Generally, when the single heater having the generally rectangular edge is maintained to a given temperature after the power supply, heat inclination occurs into the center of the heater to generate a high temperature, and thus, heat loss occurs toward the edge of the heater, so that the edge portion of the heater is heated to a lower temperature than the center of the heater. Due to such non-uniform heating, as shown in FIG. 7, radial heat distribution around the single heater is observed. On the PCR heating block where two or more rectangular heaters are repeatedly arranged, the radial heat distribution causes non-uniformity of heat between the adjacent heaters to be increased due to their heat superposition. Referring to FIG. 8, it is understood that non-uniform heat superposition occurs between the first heater 111 and the second heater 121 due to the radial heat distribution generated from the respective heaters 111 and 112. For example, such non-uniform heat superposition easily occurs on the PCR heating block having the two or more heaters repeatedly arranged under the condition that the width of each rectangular heater is about 4 mm and the distance between the adjacent heaters is about 8 mm. The non-uniform heat superposition inhibits the accurate temperature to be maintained by each heater from being formed on the PCR heating block having the two or more heaters repeatedly arranged as shown in FIGS. 1 to 4, and further, it is hard to control the temperatures of the heaters. Furthermore, the PCR is not precisely conducted to lower the PCR efficiency. So as to solve the non-uniform heat superposition occurring between the adjacent heaters, accordingly, the distance between the adjacent heaters may be sufficiently formed, and otherwise, heat insulating materials may be disposed in the space between the adjacent heaters. In this case, however, the whole size of the PCR heating block increases, thus making it hard to achieve the miniaturization and integration of the device, and further, the manufacturing process becomes complicated, thus making it hard to accomplish high economical effects.

Figure 9:
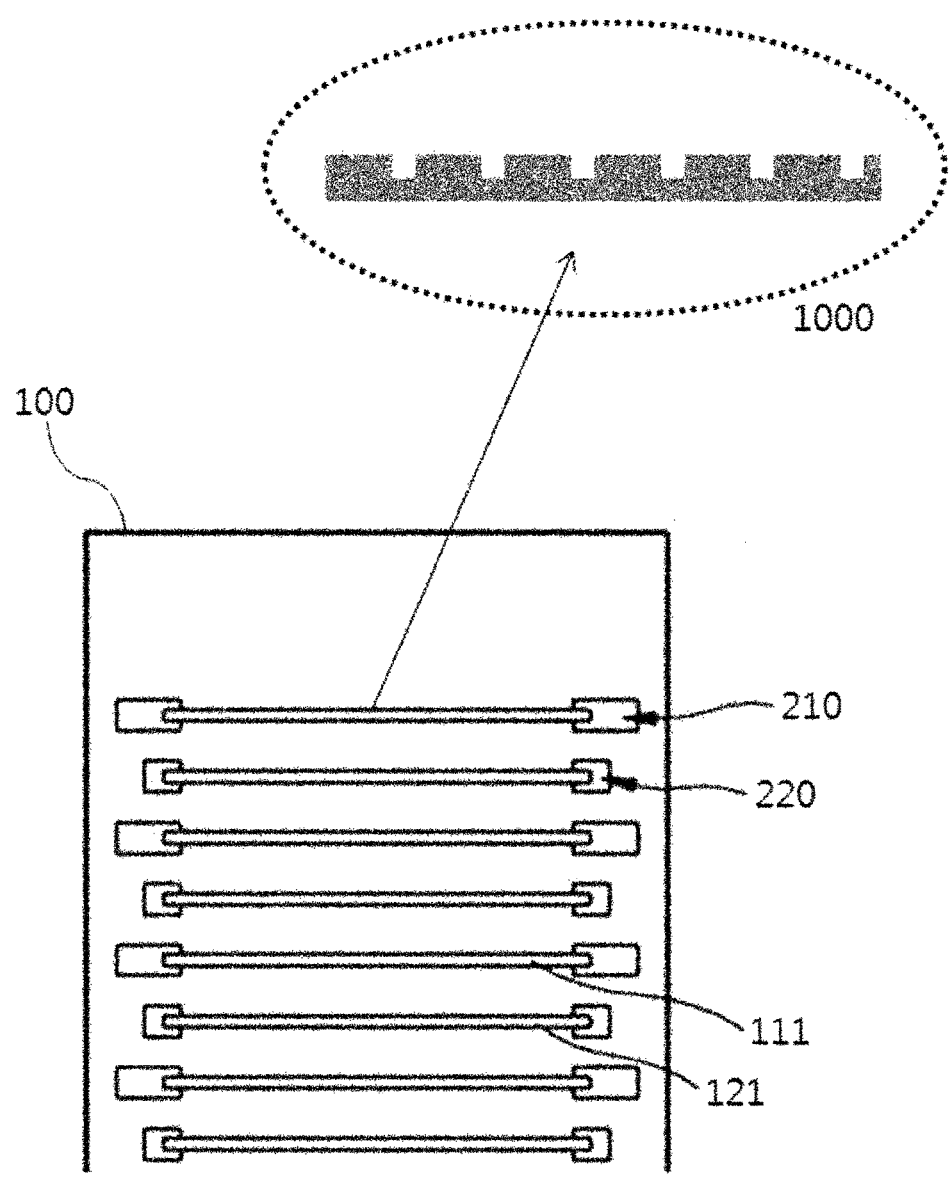
FIG. 9 depicts the PCR heating block 100 according to the first embodiment of the present invention, on which compensated patterns 1000 are formed.

FIG. 9 depicts the PCR heating block 100 according to the first embodiment of the present invention, on which compensated patterns 1000 are formed.

So as to prevent the non-uniform heat superposition between the adjacent heaters from occurring due to the radial heat distribution from the respective heaters 111 and 121, referring to FIG. 9, the PCR heating block 100 according to the present invention includes compensated patterns 1000 adapted to adjust resistances on at least portions of the heaters 111 and 121 and thus to control heat uniformity on the surfaces of the heaters 111 and 121. The compensated patterns 1000 refer to an embodied pattern structures on which the shape, material, size and arrangement of the at least portions of the rectangular heaters 111 and 121 are deformed to adjust the resistance and heat release rate on the at least portions of the heaters 111 and 121. The compensated patterns 1000 may be varied in accordance with the characteristics of the rectangular heaters 111 and 121. For example, spaces are repeatedly formed on at least a portion of each heater, thus providing a gap pattern or a wavelength pattern, and otherwise, a material on at least a portion of each heater is different from a material on the other portion thereof. Further, the size of at least a portion of each heater is different from the size of the other portion thereof, and otherwise, an arrangement of unit electrodes, that is, heater electrodes on at least a portion of each heater is different from an arrangement on the other portion thereof. Moreover, the compensated patterns 1000 may be evenly formed on the whole region of the heaters, but in some cases, they are formed just on partial regions of the heaters or formed differently according to the repeatedly arranged heaters. On the PCR heating block 100 according to the present invention, on the other hand, the heaters having the compensated patterns 1000 formed thereon are manufactured through a method selected from the group consisting of photo lithography, electro plating, shadow mask and sputter deposition, shadow mask and sputter deposition, ink jet, gravure, gravure-offset, screen printing, CNC (computerized numerically controlled) machine tool, laser beam machining, and electric discharge machining, which are conducted on the substrate.

Figure 10:
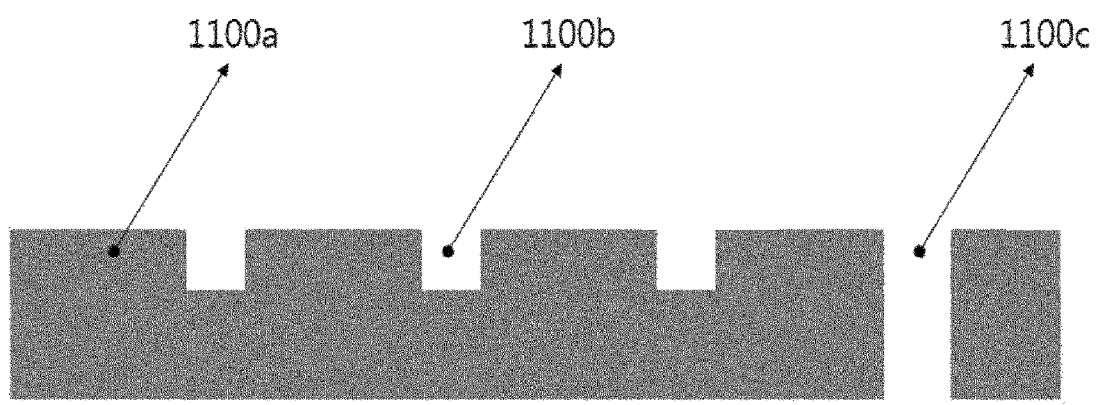
FIG. 10 depicts the compensated pattern having spaces 1100 formed on a portion of the heater 111 on the PCR heating block according to the first embodiment of the present invention.

FIG. 10 depicts the compensated pattern having spaces 1100 formed on a portion of the heater 111 on the PCR heating block according to the first embodiment of the present invention.

Referring to FIG. 10, the compensated pattern 1000 is provided with spaces 1100 repeatedly formed on at least a portion of the heater 111, thus adjusting a resistance on the heater 111 and controlling the heat uniformity on the surface of the heater 111. The spaces 1100 are formed through the deformation of the at least a portion of the heater 111 and refers to embodied patterns like concave regions, convex regions or gaps. Referring to FIG. 10, the spaces 1100 are formed in various manners on the surface of the heater 111. In this case, reference numeral 1100a indicates a convex space, reference numeral 1100b a concave space, and reference numeral 1100c indicates a gap type space. Further, the spaces 1100 are repeatedly formed on the edge surface of the heater 111 to provide a wavelength pattern, and in this case, the concave regions and the convex regions are successively and repeatedly arranged on the edge surface of the heater 111. Accordingly, a variety of shapes on the surface of the heater 111 may be formed according to various structures of the spaces 1100, so that the resistance on at least a portion of the heater 111 is adjusted to control the heat release rate of the heater 111. On the other hand, the spaces 1100 are formed to various sizes on at least one surface of the heater 111. For example, a variety of sizes or widths of the spaces 1100 are formed on a given surface of the heater 111. The sizes of the spaces 1100 are adjusted on the two or more surfaces of the heater 111 so that the resistances on at least two or more regions of the heater 111 can be adjusted, and further, the heat release rate is controlled to achieve uniform heat distribution of the heater 111.

Figure 11:
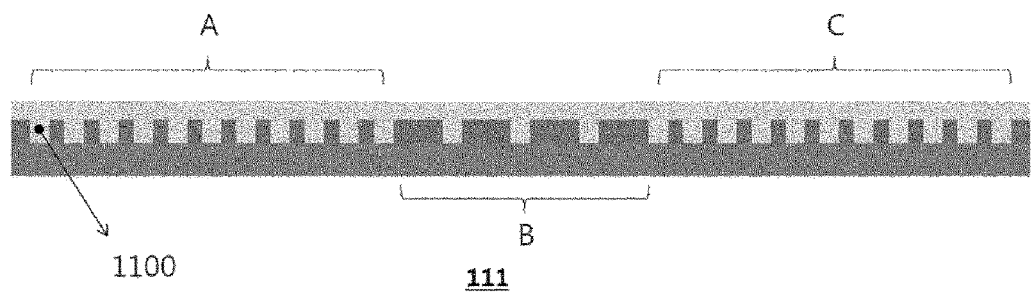
FIG. 11 depicts the compensated pattern having different line widths formed on a portion of the heater 111 on the PCR heating block according to the first embodiment of the present invention.

FIG. 11 depicts the compensated pattern having different line widths formed on a portion of the heater 111 on the PCR heating block according to the first embodiment of the present invention.

Referring to FIG. 11, the compensated pattern 1000 has the spaces 1100 formed on at least a portion of the heater 111 in such a manner as to have different line widths from each other, thus adjusting the resistance on the heater 111 and controlling the heat uniformity on the surface of the heater 111. The compensated pattern 1000, which controls the heat uniformity by the adjustment of the resistance through the line widths of the spaces 1100, is embodied by providing different line widths on at least a portion of the heater 111, deforming the resistance on at least a portion of the heater 111, and controlling the heat release rate by each position of the heater 111. The compensated pattern 1000 having different line widths of the spaces 1100 may be formed in various manners on the surface of the heater 111 on which the spaces 1100 are repeatedly formed. The compensated pattern 1000 having different line widths of the spaces 1100 may be formed evenly on the whole region of the heater 111, but in some cases, it may be formed on a partial region of the heater 111. On the other hand, the compensated pattern 1000 has different line widths on two or more given sections formed on the surface of the heater 111. That is, a plurality of sections A, B and C are defined on the surface of the heater 111, and the heat release rates of the respective sections A, B and C on the heater 111 are controlled. For example, as shown in FIG. 11, when the line widths of the convex spaces 1100 on the sections A, B and C are compared with each other on the PCR heating block 100 according to the present invention, sections A and C have smaller line widths than section B, thus having relatively high resistance to increase the heat release rates, and contrarily, section B has larger line widths than sections A and C, thus having relatively low resistance to decrease the heat release rate. As the line widths of the spaces 1100 are adjusted, accordingly, resistance becomes decreased at a portion of the rectangular heater at which the temperature is high, and resistance becomes increased at a portion of the rectangular heater at which the temperature is low, so that the heat release rates are appropriately controlled to overcome the non-uniformity of the temperature on the heater.

Figure 12:
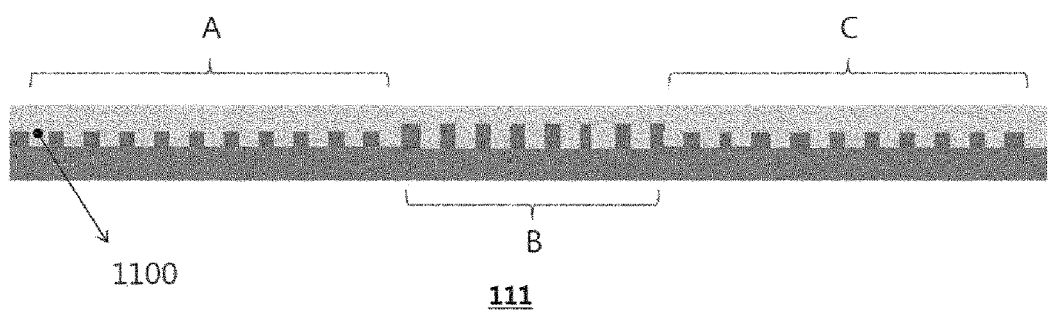
FIG. 12 depicts the compensated pattern having a different thickness formed on a portion of the heater 111 on the PCR heating block according to the first embodiment of the present invention.

FIG. 12 depicts the compensated pattern having a different thickness formed on a portion of the heater 111 on the PCR heating block according to the first embodiment of the present invention.

Referring to FIG. 12, the compensated pattern 1000 has at least a portion of the heater 111 having a different thickness, thus adjusting the resistance on the heater 111 and controlling the heat uniformity on the surface of the heater 111. The compensated pattern 1000, which has a different thickness on at least a portion of the heater 111, is embodied by providing a different thickness on at least a portion of the heater 111, deforming the resistance on at least a portion of the heater 111, and controlling the heat release rate by each position of the heater 111. For example, the compensated pattern 1000 having a different thickness on at least a portion of the heater 111 may be formed with concave surfaces and convex surfaces successively and repeatedly formed on the surface of the heater 111. In this case, the concave surfaces or the convex surfaces have different thicknesses in the range of about 0.001 µm to 1 mm, but they are not limited thereto. Further, the compensated pattern 1000 having the different thickness on at least a portion of the heater 111 may be formed evenly on the whole region of the heater 111, but in some cases, it may be formed on a partial region of the heater 111. On the other hand, the compensated pattern 1000 has different thicknesses on two or more given sections formed on the surface of the heater 111. That is, a plurality of sections A, B and C are defined on the surface of the heater 111, and the heat release rates of the respective sections A, B and C on the heater 111 are controlled. For example, according to the first embodiment of the present invention as depicted in FIG. 12, when the thicknesses of the convex surfaces on sections A, B and C are compared with each other on the PCR heating block 100, sections A and C are less thicker than section B, thus having relatively high resistance to increase the heat release rates. However, section B has a thicker thickness than sections A and C, thus having relatively low resistance to decrease the heat release rate. As the thickness on at least a portion of the heater 111 is adjusted, accordingly, the resistance decreases at a portion of the rectangular heater at which the temperature is high, and the resistance increases at a portion of the rectangular heater at which the temperature is low, so that the heat release rates are appropriately controlled to overcome the non-uniformity of the temperature on the heater.

Figure 13:
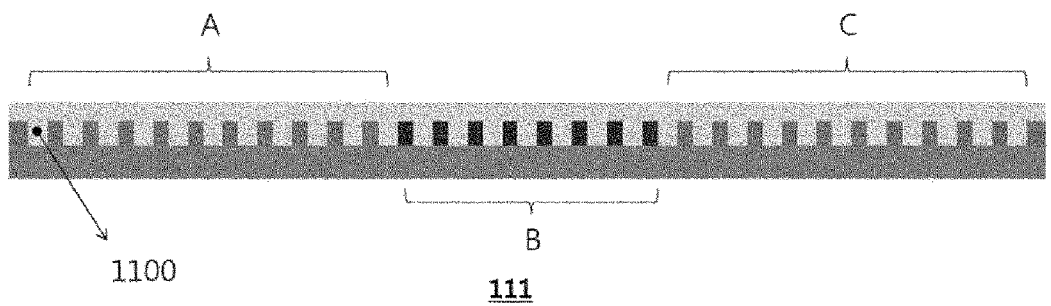
FIG. 13 depicts the compensated pattern made of a different material formed on a portion of the heater 111 on the PCR heating block according to the first embodiment of the present invention.

FIG. 13 depicts the compensated pattern made of a different material formed on a portion of the heater 111 on the PCR heating block according to the first embodiment of the present invention.

Referring to FIG. 13, the compensated pattern 1000 has at least a portion of the heater 111 made of a different material, thus adjusting the resistance on the at least a portion of the heater 111 and controlling the heat uniformity on the surface of the heater 111. The compensated pattern 1000, which has a different material on at least a portion of the heater 111, is embodied by providing a different material on at least a portion of the heater 111, deforming the resistance on at least a portion of the heater 111, and controlling the heat release rate by each position of the heater 111. The heater 111 is made of one or more materials selected from the group consisting of chrome, aluminum, copper, iron, silver, carbon, and composite materials thereof, and only if the materials are conductive, they do not matter. Further, the compensated pattern 1000 having the different material on at least a portion of the heater 111 may be formed evenly on the whole region of the heater 111, but in some cases, it may be formed on a partial region of the heater 111. On the other hand, the compensated pattern 1000 has different materials on two or more given sections formed on the surface of the heater 111. That is, a plurality of sections A, B and C are defined on the surface of the heater 111, and the heat release rates of the respective sections A, B and C on the heater 111 are controlled. For example, as shown in FIG. 13, when the materials of the convex surfaces (or the convex spaces) on sections A, B and C are compared with each other on the PCR heating block 100 according to the present invention, sections A and C are made of higher non-resistance materials than section B, thus having relatively high resistance to increase the heat release rates, and contrarily, section B is made of a lower non-resistance material than sections A and C, thus having relatively low resistance to decrease the heat release rate. As the material on at least a portion of the heater 111 is varied, accordingly, the resistance decreases at a portion of the rectangular heater at which a temperature is high, and the resistance increases at a portion of the rectangular heater at which a temperature is low, so that the heat release rates are appropriately controlled to overcome the non-uniformity of the temperature on the heater.

Figure 14:
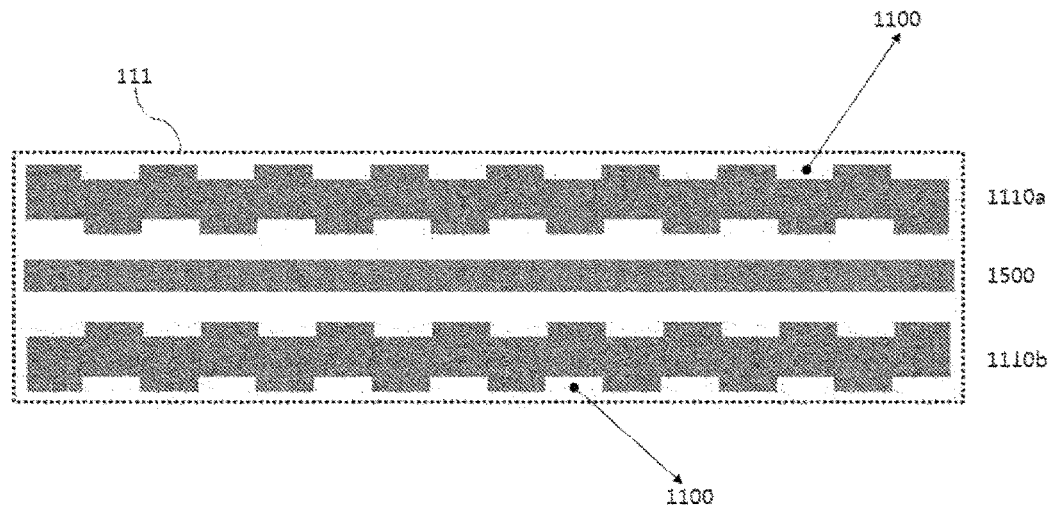
FIG. 14 depicts the compensated pattern having a different arrangement formed on a portion of the heater 111 on the PCR heating block according to the first embodiment of the present invention.

FIG. 14 depicts the compensated pattern having a different arrangement formed on a portion of the heater 111 on the PCR heating block according to the first embodiment of the present invention.

Referring to FIG. 14, the compensated pattern 1000 has at least a portion of the heater 111 having a different arrangement, thus adjusting the resistance on the at least a portion of the heater 111 and controlling the heat uniformity on the surface of the heater 111. The compensated pattern 1000 is configured to have heater electrodes 1110a and 1110b having spaces 1100, for example, convex spaces or concave spaces formed in a zigzag manner on one surface of the heater 111 and on the other surface thereof. For example, the spaces 1100 are formed in the zigzag manner on the facing surfaces of each heater electrode. Further, the PCR heating block according to the present invention may include a rectangular heater electrode 1500 and the heater electrodes 1110a and 1110b spaced apart from the rectangular heater electrode 1500 and having the compensated pattern 1000 formed thereon. Furthermore, as shown in FIG. 14, the rectangular heater electrode 1500 is disposed on the center of the heater 111, and the heater electrodes 1110a and 1110b having the compensated pattern 1000 formed thereon are spaced apart from the rectangular heater electrode 1500 in both directions in such a manner as to be symmetrically located with respect to the rectangular heater electrode 1500. That is, the PCR heating block according to the present invention may include only the heater electrodes 1110a and 1110b having the compensated pattern 1000 formed thereon, but if necessary, it may include various combinations of the heater electrodes 1110a and 1110b having the compensated pattern 1000 formed thereon and the conventional rectangular heater electrode 1500. Accordingly, the resistance decreases at a portion of the conventional rectangular heater electrode at which a temperature is high, and the resistance increases at a portion of the conventional rectangular heater electrode at which a temperature is low, so that the heat release rates are appropriately controlled to overcome the non-uniformity of the temperature on the heater.

Figure 15:
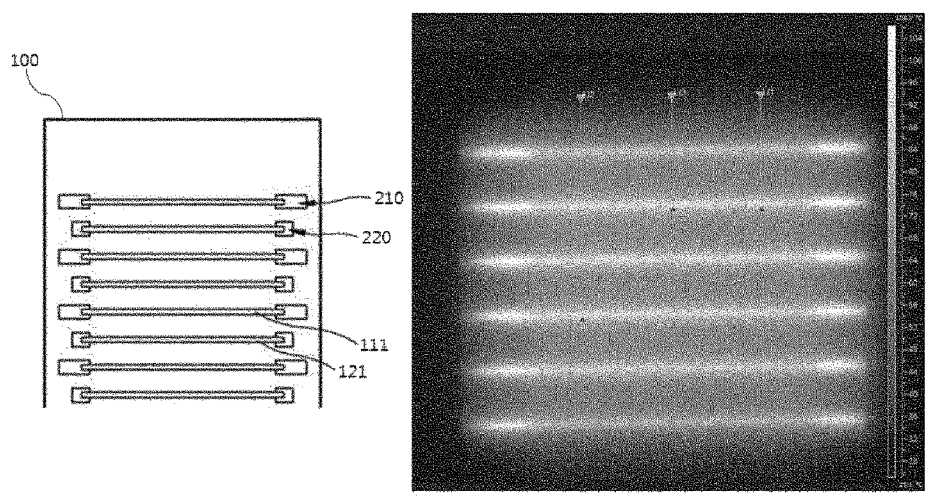
FIG. 15 is a photograph showing a heat distribution generated from the PCR heating block according to the first embodiment of the present invention.
Figure 16:
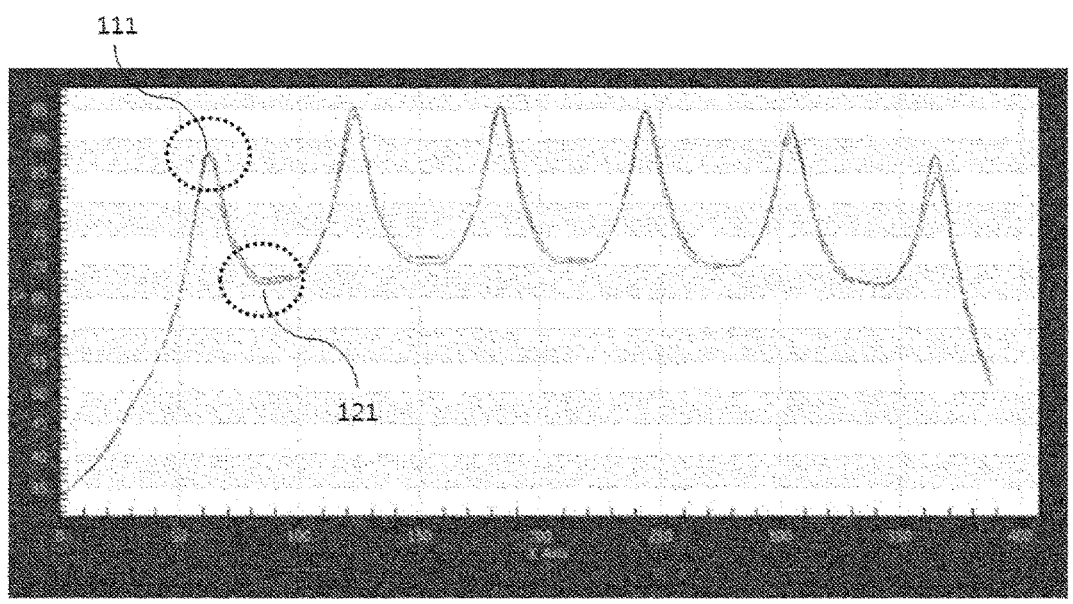
FIG. 16 is a graph showing heat distribution generated from the PCR heating block according to the first embodiment of the present invention.

FIG. 15 is a photograph showing a heat distribution generated from the PCR heating block according to the first embodiment of the present invention. FIG. 16 is a graph showing heat distribution generated from the PCR heating block according to the first embodiment of the present invention.

So as to check the improvement of the heat uniformity of the PCR heating block according to the present invention when compared with the conventional rectangular heater, the PCR heating block as shown in FIG. 11 is made. The PCR heating block is configured that the heaters are repeatedly arranged on the substrate in such a manner as to have the compensated patterns formed thereon, on which the convex spaces and the concave spaces are successively and repeatedly formed. Further, the PCR heating block is configured that the line widths of the convex spaces in the sections A and C and the distance between the convex spaces are 200 µm, and the line widths of the convex spaces in section B and the distance between the convex spaces are 400 µm, thus controlling the heat release rates on each section. In this case, the line widths of the convex spaces and the distance between the convex spaces are adjustable in the range of about 50 nm and 1 mm. The heater has a thickness of 10 μm, but may be adjustable in the range of about 10 nm to 1 mm.

Referring to FIG. 15, it can be appreciated that the heat distribution generated from the PCR heating block according to the present invention is substantially uniform when compared with the heat distribution of the conventional rectangular heater as shown in FIGS. 7 and 8. Further, referring to FIG. 16, the temperature peak points (circular dotted lines) of the first heater 111 and the adjacent second heater 121 of the PCR heating block according to the present invention are obviously distinguished, and accordingly, it can be understood that non-uniform heat superposition is substantially decreased, thus improving the heat uniformity of the heaters. Further, it can be checked that in the state where a given temperature is maintained on one heater on which the compensated pattern is formed after power has been applied to the heater, the temperature difference between the center region of the heater and the edge region of the heater is decreased to form the uniform heat distribution on the whole region of the heater. Furthermore, it can be checked that in the state where given temperatures are maintained on two or more heaters on which the compensated patterns are formed after power has been applied to the heaters, the heat uniformity between the adjacent heaters is greatly increased. In addition, the two-step PCR is conducted through the PCR heating block having the repeatedly arranged heaters on which the compensated patterns are formed, so that it can be checked that the adjacent two heaters accurately maintain the temperature (95° C.) of the denaturing step and the temperature (72° C.) of the annealing/extension step. Through the PCR heating block according to the present invention, accordingly, the precise control of the temperatures is achieved to increase the PCR efficiency during the PCR, and further, the control module can be simplified and integrated, thus accomplishing the miniaturization of the PCR device. Also, the manufacturing process becomes simple, thus providing high economical effects.

Figure 17:
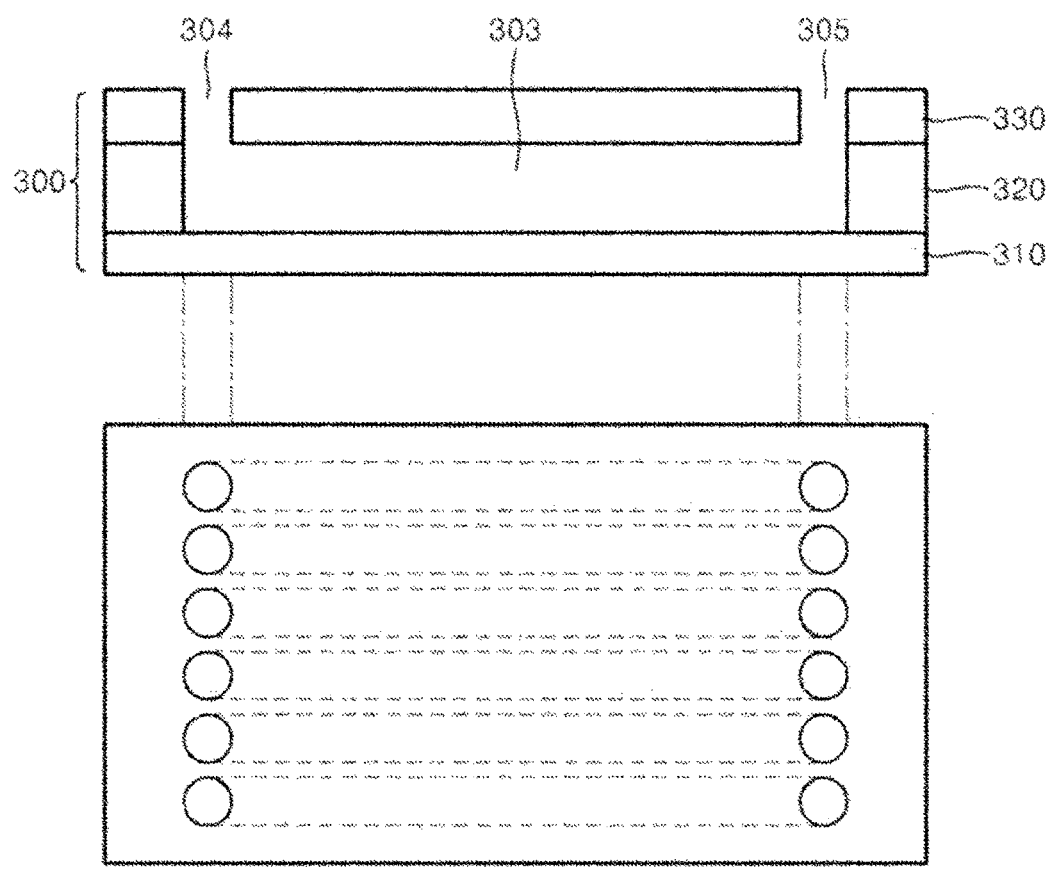
FIG. 17 depicts a PCR reaction unit 300 having thermal contact with the PCR heating block.

FIG. 17 depicts a PCR part 300 having thermal contact with the PCR heating block.

Referring to FIG. 17, a PCR reaction unit 300 includes a first plate 310 bonded or attached to the PCR heating block 100, a second plate 320 disposed on top of the first plate 310 and having one or more reaction channels 303, and a third plate 330 disposed on top of the second plate 320 and having an inlet 304 and an outlet 305 formed on both ends of each reaction channel 303. Accordingly, the PCR reaction unit 300 has a thin film-laminated structure, thus providing a simple manufacturing process and a low manufacturing cost and achieving easy heat exchanging with the PCR heating block 100. The PCR reaction unit 300 is made of various materials, and preferably, it is made of a plastic thin film. Further, the PCR reaction unit 300 is made of a light transmissive material, and if it is used for real time PCR based on optical measurements like fluorescence, phosphorescence, luminescence, Raman spectroscopy, surface enhanced Raman scattering and surface Plasmon resonance, the PCR reaction unit 300 is preferably made of a light transmissive material.

The first plate 310 is bonded or attached to the PCR heating block 100 and receives heat from the PCR heating block 100. The first plate 310 is made of various materials, and preferably, it is made of a material selected from the group consisting of polydimethylsiloxane (PDMS), cyclo-olefin copolymer (COC), polymethylmetharcylate (PMMA), polycarbonate (PC), polypropylene carbonate (PPC), polyether sulfone (PES), polyethylene terephthalate (PET), and a combination thereof. Further, hydrophilic substance (not shown) is applied to the top surface of the first plate 310 so as to serve to gently conduct the PCR. Through the application of the hydrophilic substance, accordingly, a single layer containing the hydrophilic substance is formed on the first plate 310. The hydrophilic substance includes various materials, and preferably, includes a material selected from the group consisting of carboxyl group (—COOH), amine group (—NH2), hydroxyl group (—OH), and sulfone group (—SH). The application of the hydrophilic substance is conducted in a manner known in the art.

The second plate 320 is disposed on top of the first plate 310 and has one or more reaction channels 303. The reaction channels 303 are connected to the inlets 304 and the outlets 305 formed on the third plate 330. Accordingly, a target sample solution to be amplified is introduced into the reaction channels 303, and then, the PCR is conducted. Further, two or more reaction channels may be formed in accordance with their use purpose and range, and as shown in FIG. 1, five reaction channels 303 are formed. The second plate 320 is made of various materials, and preferably, it is made of thermoplastic resin or thermosetting resin selected from the group consisting of polymethylmetharcylate (PMMA), polycarbonate (PC), cyclo-olefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoralkoxyalkane (PFA), and a combination thereof. Further, the second plate 320 has various thicknesses, and preferably, it has a thickness of 0.01 μm to 5 mm. The reaction channels 303 have various widths and lengths, and preferably, have a width of 0.001 mm to 10 mm and a length of 1 mm to 400 mm. Furthermore, the inner wall of the second plate 320 is coated with a material like silane group, bovine serum albumin (BSA) and so on, so as to prevent protein from being absorbed thereto. The application of the material is conducted in a manner known in the art.

The third plate 330 is disposed on top of the second plate 320. The third plate 330 has the inlet 304 formed on one region thereof on each reaction channel 303 formed on the second plate 320 and the outlet 305 formed on the other region thereof on each reaction channel 303. The inlet 304 is a portion into which the target sample solution containing the nucleic acid to be amplified is introduced. The outlet 305 is a portion through which the target sample solution is discharged after the completion of the PCR. Accordingly, the third plate 330 covers one or more reaction channels 303 formed on the second plate 320, while allowing the inlets 304 and the outlets 305 to serve as the inlets and outlets of one or more reaction channels 303. Further, the third plate 330 is made of various materials, and preferably, it is made of a material selected from the group consisting of polydimethylsiloxane (PDMS), cyclo-olefin copolymer (COC), polymethylmetharcylate (PMMA), polycarbonate (PC), polypropylene carbonate (PPC), polyether sulfone (PES), polyethylene terephthalate (PET), and a combination thereof. Further, the inlet 304 has various sizes, and preferably, it has a diameter of 0.001 to 10 mm. Furthermore, the outlet 305 has various sizes, and preferably, it has a diameter of 0.001 to 10 mm. In addition, cover means (not shown) are mounted on the inlet 304 and the outlet 305 so as to prevent the target sample solution from leaking when the PCR for the target sample solution is conducted on one or more reaction channels 303. The cover means have various shapes, sizes or materials. Further, the third plate 330 has various thicknesses, and preferably, it has a thickness of 0.001 to 10 mm. On the other hand, two or more inlets 304 and outlets 305 may be formed on the third plate 330.

The PCR reaction unit 300 is easily made through a method including the steps of: providing the third plate 330 having the inlets 304 and the outlets 305 formed by means of machining, forming one or more reaction channels 303 by means of machining over portions corresponding to the inlets 304 and the outlets 305 of the third plate 330 on a plate having the corresponding size to the underside surface of the third plate 330 to provide the second plate 320, forming a surface containing the hydrophilic substance by means of surface treatment on the top surface of a plate having the corresponding size to the underside surface of the second plate 320 to provide the first plate 310, and bonding the underside surface of the third plate 330 to the top surface of the second plate 320 and bonding the underside surface of the second plate 320 to the top surface of the first plate 310.

The inlets 304 and the outlets 305 of the third plate 330 and one or more reaction channels 303 of the second plate 320 are formed by means of a machining method selected from the group consisting of injection molding, hot-embossing, casting, and laser ablation. Further, the hydrophilic substance on the surface of the first plate 310 is applied thereto by means of a method selected from the group consisting of oxygen and argon plasma treatment, corona discharge, and surface active agent coating, and the application of the hydrophilic substance is conducted in a manner known in the art. Also, the bonding of the underside surface of the third plate 330 to the top surface of the second plate 320 and the bonding of the underside surface of the second plate 320 to the top surface of the first plate 310 are conducted by means of thermal bonding, ultrasonic welding, solvent bonding, hot plate welding, ultraviolet bonding, and press bonding in a manner known in the art. Further, a double-sided adhesive, a thermoplastic resin or a thermosetting resin (which is not shown) may be applied to the space between the third plate 330 and the second plate 320 and between the second plate 320 and the first plate 310.

Figure 18:
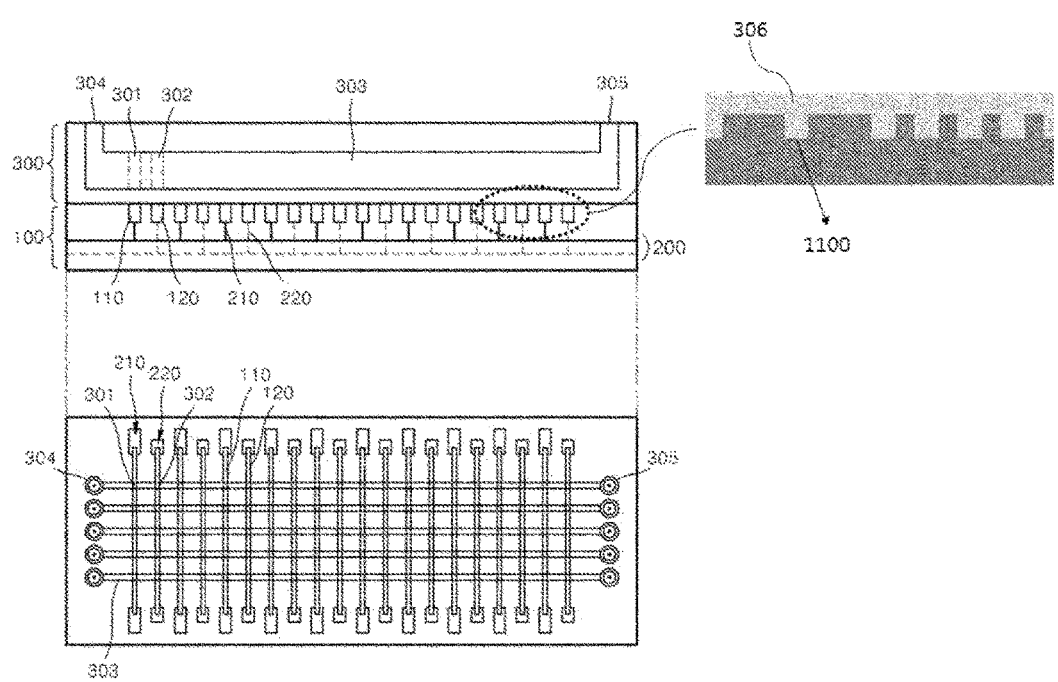
FIG. 18 depicts a PCR chip, which integrally coupled between the PCR heating block and the PCR reaction unit.
Figure 19:
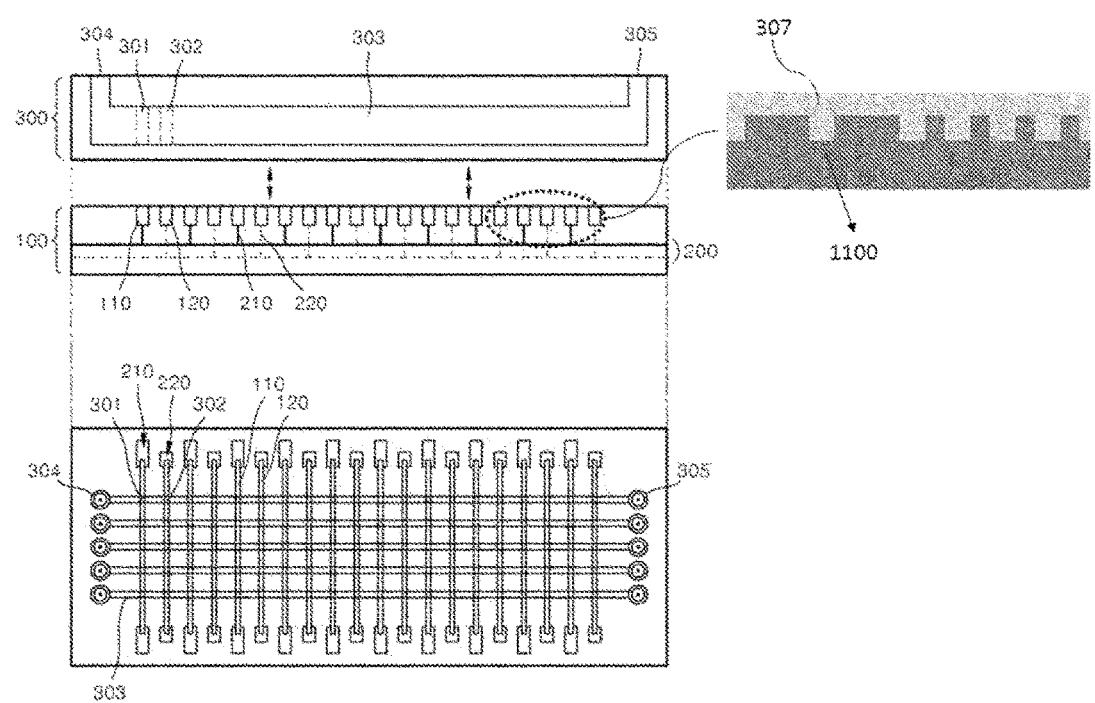
FIG. 19 depicts a PCR chip, which has the PCR heating block and the PCR reaction unit as a separate element.

FIG. 18 depicts a PCR chip, which integrally coupled between the PCR heating block and the PCR part. FIG. 19 depicts a PCR chip, which has the PCR heating block and the PCR part as a separate element.

The PCR heating block having the compensated patterns according to the present invention is applicable to various PCR modules or devices. For example, the PCR heating block having the compensated patterns is mounted on the PCR reaction unit into which the PCR solution is accommodated, thus providing a PCR chip (having an internal chip as shown in FIG. 18), and otherwise, it is in thermal contact with or separate from a PCR chip having the PCR reaction unit, thus providing a PCR device (having an external chip as shown in FIG. 19). In case of the internal chip, an insulator 306 is formed on the top surface of the PCR heating block 100 having the compensated patterns to prevent the occurrence of electrolysis of the PCR solution, and in case of the external chip, a heater protection insulator 307 is formed on a top surface of the PCR heating block 100 having the compensated patterns. The insulators 306 and 307 preferably have a thickness of about 20 μm, and they have a thickness in the range of about 50 nm to 1 mm. The insulators 306 and 307 are made of various materials capable of preventing an occurrence of electrolysis of the PCR solution, and for example, they are made of a material selected from the group consisting of oxide, nitride, thermosetting resin, thermoplastic resin, and ultraviolet curing resin. In more detail, the oxide is selected from the group consisting of silicon oxide ($SiO_2$), titanium oxide ($TiO_2$), aluminum oxide ($Al_2O_3$), hafnium oxide ($HfO_2$), vanadium oxide ($V_3O_4$), zirconium oxide ($ZrO_2$), antimony oxide ($Sb_2O_3$), and yttrium oxide ($Y_2O_3$), and the nitride is selected from the group consisting of silicon nitride ($Si_3N_4$), titanium nitride (TiN), aluminum nitride (AlN), tantalum nitride ($Ta_3N_5$), hafnium nitride (HfN), vanadium nitride (VN), and zirconium nitride (ZrN). The thermosetting resin is selected from the group consisting of phenol resin, epoxy resin, urea resin, melamine resin, alkyd resin, polyester resin, aniline, polyimide, and silicone resin, and the thermoplastic resin is selected from the group consisting of polyethylene, polyvinyl chloride resin, polystyrene, polyamide resin, polytetrafluorethylene, polypropylene. The ultraviolet curing resin is selected from the group consisting of epoxy acrylate, polyester acrylate, urethane acrylate, polybutadiene acrylate, silicone acrylate, and alkyl acrylate. On the other hand, the insulators 306 and 307 are formed on the top surface of the PCR heating block by a method selected from the group consisting of photo lithography, electro plating, shadow mask and evaporator deposition, shadow mask and sputter deposition, ink jet, gravure, gravure-offset, and screen printing.

Figure 20:
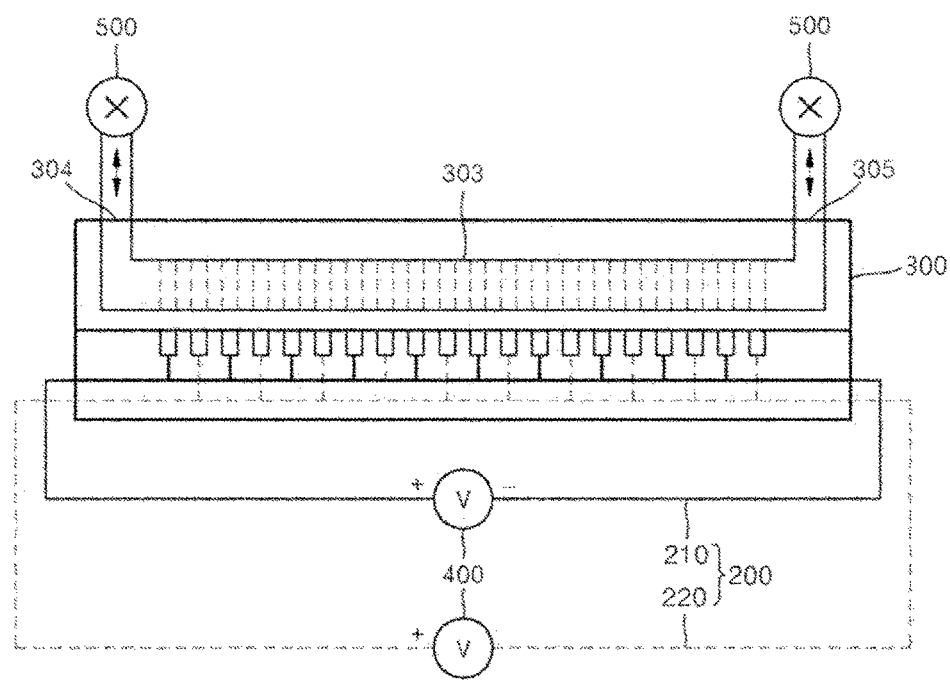
FIG. 20 depicts a PCR conducted by the PCR device having the PCR heating block 100 on which the heaters having the compensated patterns formed thereon are repeatedly arranged.

FIG. 20 depicts a PCR conducted by the PCR device having the PCR heating block 100 on which the heaters having the compensated patterns formed thereon are repeatedly arranged.

Referring to FIG. 20, the PCR device according to the present invention includes a PCR reaction unit 300, a power supply source 400 and pumps 500. In more detail, the PCR reaction unit 300 comes into contact with the PCR heating block.

The power supply source 400 is a module supplying power to the power supply part 200 and connected correspondingly to the first distributed wire 210 and the second distributed wire 220 of the power supply part 200. While the PCR is being conducted, for example, the first power port (not shown) of the power supply source 400 is electrically connected to the first distributed wire 210, and a second power port (not shown) of the power supply source 400 is electrically connected to the second distributed wire 220. After that, if a command for conducting the PCR is issued from a user, the power supply source 400 supply power to the first distributed wire 210 and the second distributed wire 220 and rapidly heats the first heaters and the second heaters of the PCR heating block. If the heaters reach given temperatures, further, the power supply source 400 controls the quantity of power supplied to allow the heaters to maintain the given temperatures. For example, the given temperature at each first heater is a temperature of the PCR denaturing step (in the range of 85 to 105° C., preferably 95° C.), and the given temperature at each second heater is a temperature of the PCR annealing/extension step (in the range of 50 to 80° C., preferably 72° C.). Otherwise, the given temperature at each first heater is a temperature of the PCR annealing/extension step (in the range of 50 to 80° C., preferably 72° C.), and the given temperature at each second heater is a temperature of the PCR denaturing step (in the range of 85 to 105° C., preferably 95° C.).

The pumps 500 are modules controlling the flow rate of the solution flowing in one or more reaction channels 303 of the PCR reaction unit 300, and they may provide positive pressure or negative pressure. For example, they may be syringe pumps. The pumps 500 are operably disposed on portions of the reaction channels 303, and preferably, they are connected to the inlets 304 and/or the outlets 305 formed on both ends of the reaction channels 303. If the pumps 500 are connected to the inlets 304 and/or the outlets 305 formed on both ends of the reaction channels 303, further, they serve as stoppers preventing the target sample solution from leaking through the inlets 304 and/or the outlets 305. Furthermore, if the flow rate of the fluid, that is, the target sample solution flowing in each reaction channel 303 is to be controlled in one direction, one pump 500 is connected only to either the inlet 304 or the outlet 305, and a general stopper is sealingly connected to the other not connected to the pump 500. Contrarily, if the flow rate of the fluid, that is, the target sample solution flowing in each reaction channel 303 is to be controlled in both directions, the pumps 500 are connected to both of the inlet 304 and the outlet 305.

The nucleic acid amplification reaction of the PCR solution in the PCR device having the PCR reaction unit 300, the power supply source 400 and the pumps 500 is conducted by the steps as follows.

At a first step, the PCR solution is prepared having desired double-stranded target DNA, oligonucleotide primer having the complimentary sequence to specific sequence to be amplified, DNA polymerase, deoxyribonucleotide triphosphates (dNTP), and PCR buffer.

At a second step, the PCR solution is introduced into the PCR reaction unit 300. In this case, the PCR solution is supplied to each reaction channel 303 of the PCR reaction unit 300 through the inlet 304.

At a third step, the power supply part 200, that is, the first distributed wire 210 and the second distributed wire 220 are connected to the power supply source 400, and the inlets 304 and the outlets 305 of the PCR reaction unit 300 have a sealing connection to the pumps 500.

At a fourth step, power supply is commanded to the power supply source 400 to heat the first heaters and the second heaters through the first distributed wire 210 and the second distributed wire 220 so that the first heaters maintain a given temperature (95° C.) of the PCR denaturing step, and the second heaters maintain a given temperature (72° C.) of the PCR annealing/extension step.

At a fifth step, lastly, the positive pressure is provided by the pumps 500 connected to the inlets 304 or the negative pressure is provided by the pumps 500 connected to the outlets 305, so that the target sample solution flows horizontally in the reaction channels 303. In this case, the flow rate of the PCR solution is controllable by the adjustment of the positive pressure and the negative pressure provided by the pumps 500.

Through the above-mentioned steps, the PCR solution flows longitudinally along the portions corresponding to the upper side portions of the first heaters and the portions corresponding to the upper side portions of the second heaters from the end of the inlet 304 of each reaction channel 303 to the end of the outlet 305 thereof, thus conducting the PCR. Referring to FIG. 20, the PCR solution receives the heat from the PCR heating block 100 on which the heater units having the first heaters and the second heaters are repeatedly arranged 10 times and is passed through the PCR denaturing step on the portions corresponding to the upper side portions of the first heaters and through the PCR annealing/extension step on the portions corresponding to the upper side portions of the second heaters, thus finishing 10 PCR cycles. After that, the PCR solution reversely flows longitudinally along the portions corresponding to the upper side portions of the first heaters and the portions corresponding to the upper side portions of the second heaters from the end of the outlet 305 of each reaction channel 303 to the end of the inlet 304 thereof, thus selectively conducting the PCR again.

Figure 21:
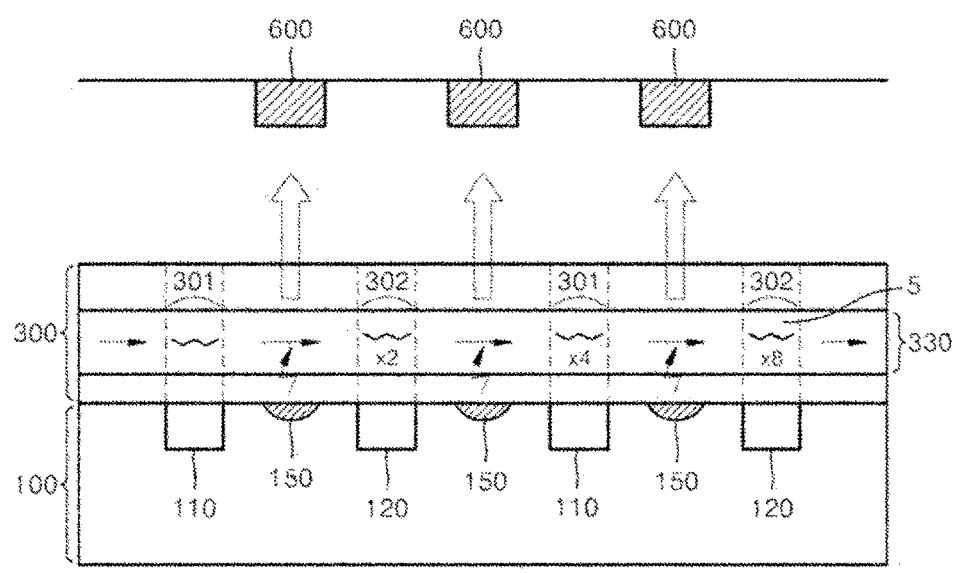
FIG. 21 depicts optical real time PCR conducted by a PCR device having the PCR heating block 100 on which the heaters having the compensated patterns formed thereon and repeatedly arranged, light sources 150, and light detectors 600.

FIG. 21 depicts optical real time PCR conducted by a PCR device having the PCR heating block 100 on which the heaters having the compensated patterns formed thereon and repeatedly arranged, light sources 150, and light detectors 600.

Referring to FIG. 21, the PCR device according to the present invention includes the PCR reaction unit 300 made of a light transmissive material, the PCR heating block 100 having light sources 150 disposed between the first heaters 110 and the second heaters 120, power supply parts 400, pumps 500, and light detectors 600.

As shown, the PCR reaction unit 300 is made of a light transmissive material, and the PCR heating block 100 has the light sources 150 disposed between the first heater 110 and the second heater 120. Further, the PCR device includes the light detectors 600 adapted to detect the light emitted from the light sources 150. Accordingly, the PCR device can measure and analyze the nucleic acid amplification during the PCR in real time. In this case, a fluorescent material is added to the PCR solution and emits light therefrom by light having a specific wavelength according to the production of PCR products, thus generating optical signals to be measurable and analyzable. The light sources 150 are selected from the group consisting of mercury arc lamp, xenon arc lamp, tungsten arc lamp, metal halide arc lamp, metal halide fiber, and light-emitting diodes. Further, the light sources 150 have wavelengths in the range of about 200 to 1300 nm, and otherwise, they have multi-wavelength through multiple light sources or filters. The light detectors 600 are selected from the group consisting of charge-coupled device (CCD), charge-injection device (CID), complementary-metal-oxide-semiconductor detector (CMOS), and photo multiplier tube (PMT). According to the present invention, the light sources 150 are disposed on the spaces between the first heaters 110 and the second heaters 120. Further, the light sources 150 are operably connected to lenses (not shown) collecting the light emitted from the light sources 150 and optical filters (not shown) filtering the light having specific wavelength band.

Accordingly, the nucleic acid amplification reaction can be monitored through the PCR device as shown in FIG. 21 in real time. For example, the PCR solution is successively passed through portions 301 corresponding to the upper side portions of the first heaters 110 and portions 302 corresponding to the upper side portions of the second heaters 120 in each reaction channel 303, thus conducting the PCR denaturing step and the PCR annealing/extension step. In this case, the PCR solution is passed through portions corresponding to the upper sides of the light sources 150 disposed between the first heater 110 and the second heater 120 and between the heater units each having the first heater 110 and the second heater 120. When the PCR solution is passed through portions corresponding to the upper sides of the light sources 150, the PCR solution flows slowly or momentarily stops through control, and at this time, light is emitted from the light sources 150 in such a manner as to be passed through the PCR reaction unit 300 made of the light transmissive material, that is, the reaction channels 303. After that, the optical signals generated by the nucleic acid amplification in the reaction channels 303 are measured and analyzed by means of the light detectors 600. During the PCR cycles, accordingly, the reaction results of the nucleic acid (coupled to the fluorescent material) amplification in the reaction channels 303 are monitored in real time, thus allowing the quantity of target DNA to be measured and analyzed in real time.

FIGS. 22 to 25 depicts another type of PCR part having thermal contact with the PCR heating block of FIGS. 12 to 16.

Figure 22:
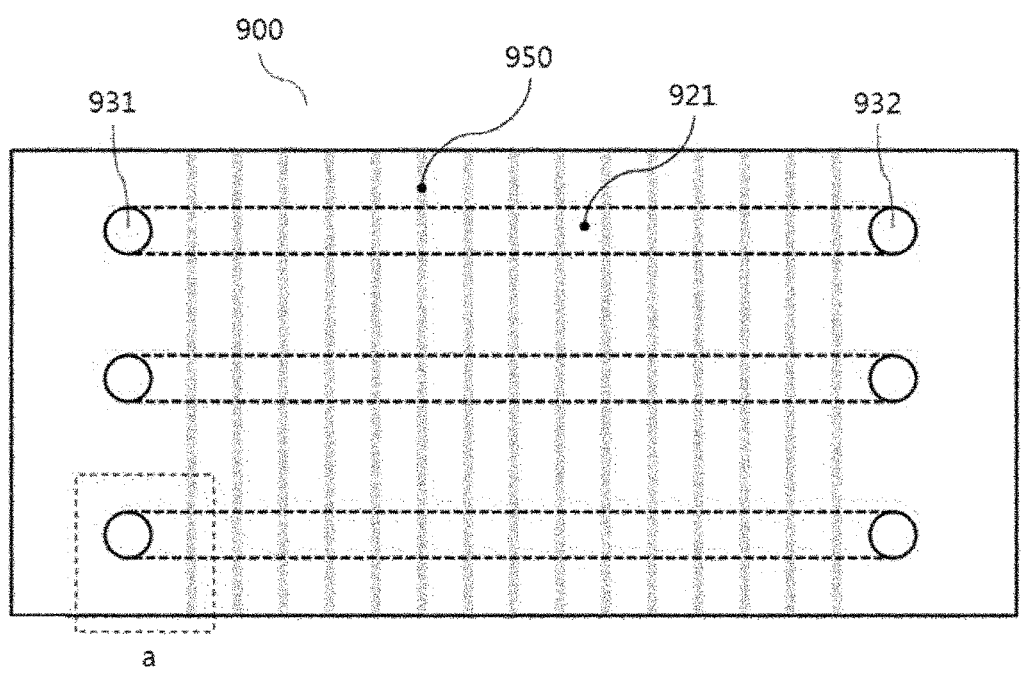
FIGS. 22 to 25 depicts another type of PCR reaction unit having thermal contact with the PCR heating block of FIGS. 12 to 16.

A PCR reaction unit 900 as shown in FIGS. 22 to 25 includes detection electrodes 950 spaced apart from each other in such a manner as to traverse the undersides of one or more reaction channels 921 in longitudinal directions of the reaction channels 921 so as to detect electrochemical signals generated from bonding of amplified nucleic acid to a redox indicator from the interiors of the reaction channels 921. When the detection electrodes 950 come into contact with the PCR heating block 100, they are located between the two or more heater groups. The PCR reaction unit 900 has a shape of a plate and includes one or more reaction channels 921 each having an inlet 931 and an outlet 932 formed on both ends thereof and the detection electrodes 950 spaced apart from each other in such a manner as to traverse the undersides of one or more reaction channels 921 in the longitudinal directions of the reaction channels 921 so as to detect electrochemical signals generated from the bonding of the amplified nucleic acid to the redox indicator from the interiors of the reaction channels 921. In this case, the detection electrodes 950 are located between the two or more heater groups 110, 120, and 130 when they come into contact with the PCR heating block 100. The PCR reaction unit 900 contains a solution having nucleic acid, for example, template nucleic acid double-stranded DNA as a PCR sample, and oligonucleotide primer having the complimentary sequence to specific sequence to be amplified, DNA polymerase, deoxyribonucleotide triphosphates (dNTP), and PCR buffer as PCR reagents. Accordingly, the PCR reaction unit 900 includes the inlets 931 introducing the sample and reagents thereinto, the outlets 932 discharging the solution after the nucleic acid amplification reaction is finished therefrom, and the reaction channels 921 conducting the nucleic acid amplification reaction of the sample and reagents. Referring to FIG. 22, the reaction channels 921 are extended to pass through the portions corresponding to the upper side portions of the first heaters and the portions corresponding to the upper side portions of the second heaters in the longitudinal direction. The PCR reaction unit 900 receives heat from the PCR heating block 100 so that the PCR sample and reagents contained in the reaction channels 921 of the PCR reaction unit 900 can be heated and maintained to given temperatures. Further, the PCR reaction unit 900 has a shape of a plate, thus enhancing thermal conductivity and providing the two or more reaction channels 921. Further, the PCR reaction unit 900 is made of a transparent or opaque plastic material, and accordingly, the thickness of the PCR reaction unit 900 is easily adjusted according to the characteristics of the plastic material, thus increasing the heat transmission efficiency and achieving the simplification of manufacturing process and the reduction of manufacturing cost.

On the other hand, the redox indicator is chemically reacted (bonded) to the amplified nucleic acid and thus generates electrochemical signals, and the electrochemical signals are successively detected and measured according to the continuous amplification of the nucleic acid. For example, the double-stranded DNA generally has negative charge, and if the redox indicator has positive charge, the amplified nucleic acid is reacted to the redox indicator according to the continuous amplification of the nucleic acid to produce the detectable signals through the variations of total quantity of charge. Accordingly, the electrochemical signals are generated by the variations of total current values caused by the bonding of the negative charge of the amplified nucleic acid and the positive charge of the redox indicator, and the redox indicator may be a cationoid among the ionized products of an ionic bonding substance. In more detail, the ionic bonding substance is methylene blue, and the redox indicator is a cationoid among the ionized products of the methylene blue. If the methylene blue $C_{16}H_{18}N_3SCl.3H_2O$ is melted in a solvent, it becomes ionized to $C_{16}H_{18}N_3S^+$ and $Cl^-$ and has positive charge by sulfur S. The double-stranded DNA consists of sugar, base, and phosphate, and the phosphate generally has negative charge. Accordingly, the double-stranded DNA has negative charge. The positive ion of methylene blue is bonded to phosphate of DNA, so that the apparent diffusion rate of methylene blue bonded to the double-stranded DNA becomes more decreased than that of methylene blue, and accordingly, the peak value of the current is reduced. During the PCR cycles, accordingly, the double-stranded DNA is amplified and the quantity of methylene blue bonded to the double-stranded DNA is increased, thus reducing the peak value of current, so that the quantity of the amplified nucleic acid can be in real time measured through the electrical signals generated by the chemical bonding of the real time amplified PCR products and the methylene blue.

Figure 23:
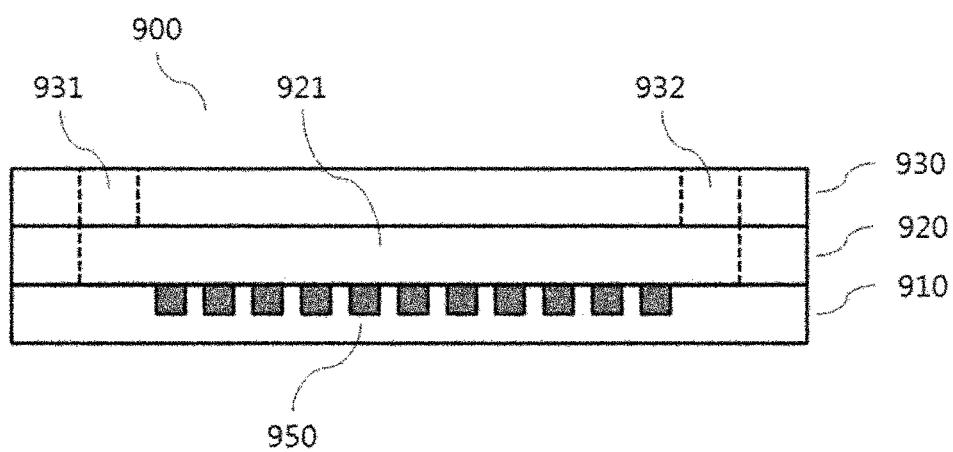

The detection electrodes 950 are made of various materials capable of detecting the electrochemical signals generated by means of the bonding of the amplified nucleic acid with the redox indicator from the interiors of the reaction channels 921. For example, the detection electrodes 950 are made of one or more materials selected from the group consisting of Au, Co, Pt, Ag, carbon nanotube, graphene, and carbon. The detection electrodes 950 are repeatedly spaced apart from each other in such a manner as to traverse the undersides of reaction channels 921 in the longitudinal directions of the reaction channels 921, and when the detection electrodes 950 come into contact with the PCR heating block 100, they are located between the two or more heater groups 110, 120 and 130. Referring to FIG. 22, the detection electrodes 950 are repeatedly spaced apart from each other on the region of each reaction channel 921 from the inlet 931 to the outlet 932, and under the above structure, they are passed through the reaction channels 921 in the longitudinal directions of the reaction channels 921, thus repeatedly detecting the electrochemical signals generated from the successively amplified nucleic acid. Moreover, as shown in FIG. 23, the detection electrodes 950 are disposed on the undersides of the reaction channels 921. On the other hand, as shown in FIG. 23, the PCR reaction unit 900 is divided largely into three layers with respect to the vertical section thereof. The PCR reaction unit 900 includes a first plate 910 on which the detection electrodes 950 are disposed, a second plate 920 disposed on top of the first plate 910 and having one or more reaction channels 921, and a third plate 930 disposed on top of the second plate 920 and having the inlets 931 and the outlets 932 formed thereon.

The top surface of the first plate 910 on which the detection electrodes 950 are disposed is bonded to the underside surface of the second plate 920. The first plate 910 is bonded to the second plate 920 having the reaction channels 921, thus ensuring the space for the reaction channels 921 and further allowing the detection electrodes 950 to be disposed on at least one region (surface) of the reaction channels 921. On the other hand, the first plate 910 is made of various materials, and preferably, it is made of a material selected from the group consisting of polydimethylsiloxane (PDMS), cyclo-olefin copolymer (COC), polymethylmetharcylate (PMMA), polycarbonate (PC), polypropylene carbonate (PPC), polyether sulfone (PES), polyethylene terephthalate (PET), and a combination thereof. Further, a hydrophilic substance (not shown) is applied to the top surface of the first plate 910 so as to serve to gently conduct the PCR. Through the application of the hydrophilic substance, accordingly, a single layer containing the hydrophilic substance is formed on the first plate 910. The hydrophilic substance includes various materials, and preferably, it includes a material selected from the group consisting of carboxyl group (—COOH), amine group (—NH2), hydroxyl group (—OH), and sulfone group (—SH). The application of the hydrophilic substance is conducted in a manner known in the art.

The top surface of the second plate 920 is bonded to the underside surface of the third plate 930. The second plate 920 includes the reaction channels 921. The reaction channels 921 are connected to the inlets 931 and the outlets 932 formed on the third plate 930. Accordingly, the PCR sample and reagents are introduced into the reaction channels 921, and next, the PCR is conducted. Further, two or more reaction channels 921 may be formed in accordance with their use purpose and range. The second plate 920 is made of various materials, and preferably, it is made of thermoplastic resin or thermosetting resin selected from the group consisting of polymethylmetharcylate (PMMA), polycarbonate (PC), cyclo-olefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoralkoxyalkane (PFA), and a combination thereof. Further, the second plate 920 has various thicknesses, and preferably, it has a thickness of 10 to 2000 μm. The reaction channels 921 have various widths and lengths, and preferably, have a width of 0.001 mm to 10 mm and a length of 1 mm to 400 mm. Furthermore, the inner wall of the second plate 920 is coated with a material like silane group material, bovine serum albumin (BSA) and so on so as to prevent DNA and protein from being absorbed thereto.

The underside surface of the third plate 930 is disposed on top of the second plate 920. The third plate 930 has the inlets 931 formed on one region of the reaction channels 921 formed on the second plate 920 and the outlets 932 formed on the other region of the reaction channels 921. The inlets 931 are portions into which the PCR sample and reagents are introduced. The outlets 932 are portions through which the PCR products after the completion of the PCR are discharged. Accordingly, the third plate 930 covers the reaction channels 921 formed on the second plate 920, while allowing the inlets 931 and the outlets 932 to serve as the inlets and outlets of the reaction channels 921. Further, the third plate 930 is made of various materials, and preferably, it is made of a material selected from the group consisting of polydimethylsiloxane (PDMS), cyclo-olefin copolymer (COC), polymethylmetharcylate (PMMA), polycarbonate (PC), polypropylene carbonate (PPC), polyether sulfone (PES), polyethylene terephthalate (PET), and a combination thereof. Further, the inlets 931 have various sizes, and preferably, they have a diameter of 1.0 to 3.0 mm. Furthermore, the outlets 932 have various sizes, and preferably, they have a diameter of 1.0 to 1.5 mm. In addition, cover means (not shown) are mounted on the inlets 931 and the outlets 932 so as to prevent the PCR sample and reagents from leaking when the PCR for the PCR sample and reagents is conducted on the reaction channels 921. The cover means have various shapes, sizes or materials. Further, the third plate 930 has various thicknesses, and preferably, it has a thickness of 0.1 to 2.0 mm. On the other hand, two or more inlets 931 and outlets 932 may be formed on the third plate 930.

On the other hand, the PCR reaction unit 900 is easily made through a method including the steps of providing the third plate 930 having the inlets 931 and the outlets 932 formed by machining, forming the reaction channels 921 by machining over portions corresponding to the inlets 931 and the outlets 932 of the third plate 930 on a plate having the corresponding size to the underside surface of the third plate 930 to provide the second plate 920, forming a surface containing the hydrophilic substance by surface treatment on the top surface of a plate having the corresponding size to the underside surface of the second plate 920 to provide the first plate 910, and bonding the underside surface of the third plate 930 to the top surface of the second plate 920 and bonding the underside surface of the second plate 920 to the top surface of the first plate 910. The inlets 931 and the outlets 932 of the third plate 930 and the reaction channels 921 of the second plate 920 are formed by machining selected from the group consisting of injection molding, hot-embossing, casting, and laser ablation. Further, the hydrophilic substance on the surface of the first plate 910 is applied thereto by a method selected from the group consisting of oxygen and argon plasma treatment, corona discharge, and surface active agent coating, and the application of the hydrophilic substance is conducted in a manner known in the art. Also, the bonding of the underside surface of the third plate 930 to the top surface of the second plate 920 and the bonding of the underside surface of the second plate 920 to the top surface of the first plate 910 are conducted by thermal bonding, ultrasonic welding, solvent bonding, hot plate welding, ultraviolet bonding, and press bonding in a manner known in the art. Further, a double-sided adhesive, a thermoplastic resin or a thermosetting resin (which is not shown) may be applied to the spaces between the third plate 930 and the second plate 920 and between the second plate 920 and the first plate 910.

Figure 24:
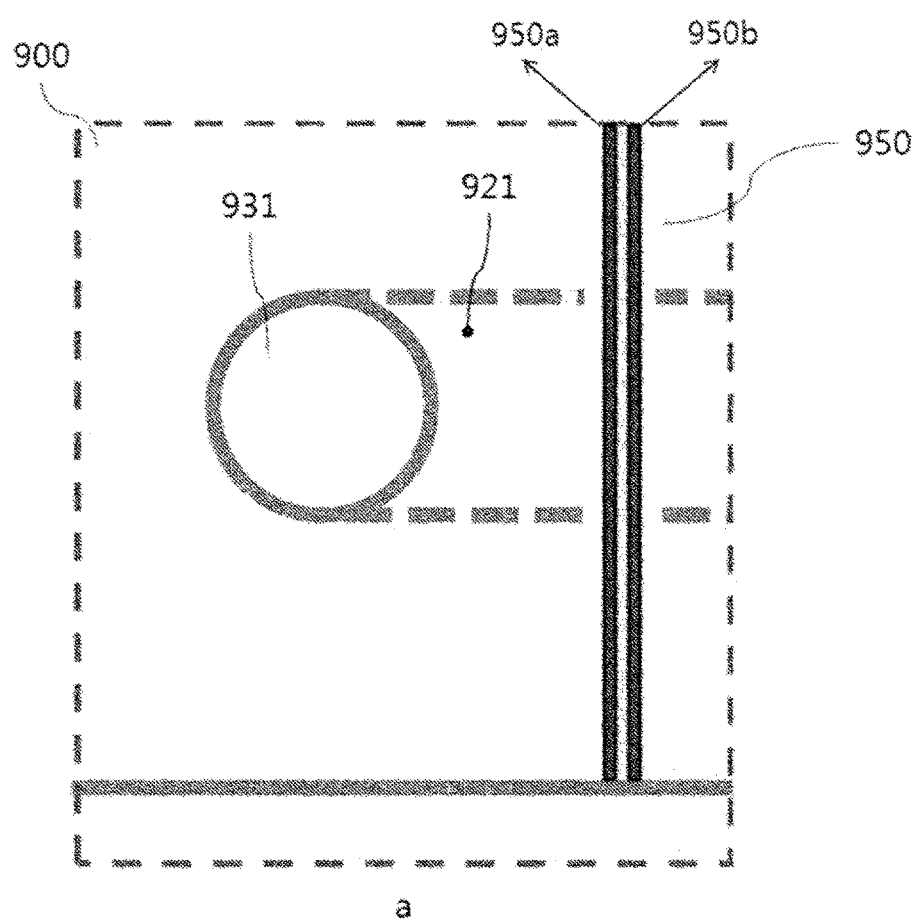
Figure 25:
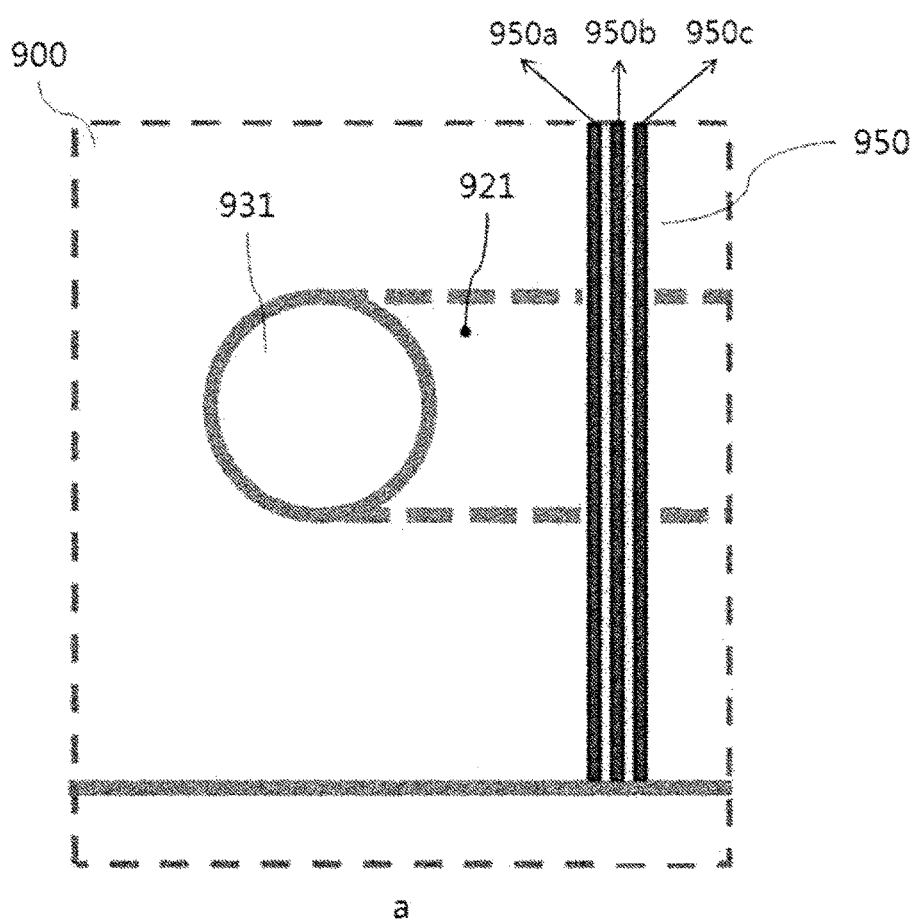

Referring to FIGS. 24 and 25 illustrating an enlarged portion "a" of FIG. 22, on the other hand, the detection electrodes 950 are provided in various manners. Referring to FIG. 24, for example, each detection is formed of a two-electrode module including a working electrode 950a on which the amplified nucleic acid and the redox indicator are bonded to each other and a reference electrode 950b on which bonding between the amplified nucleic acid and the redox indicator does not occur so that it is functioned as a measuring reference of electrode potential. Referring to FIG. 25, for example, each detection electrode 950 is formed of a three-electrode module including the working electrode 950a, the reference electrode 950b, and the counter electrode 950c along which the current generated from the working electrode 950a flows. If the detection electrode 950 is configured as a multiple electrode module, like this, the sensitivity of the electrochemical signals generated in the reaction channels 921 can be enhanced, and further, the detection and measurement of the generated signals can be easily conducted.

Figure 26:
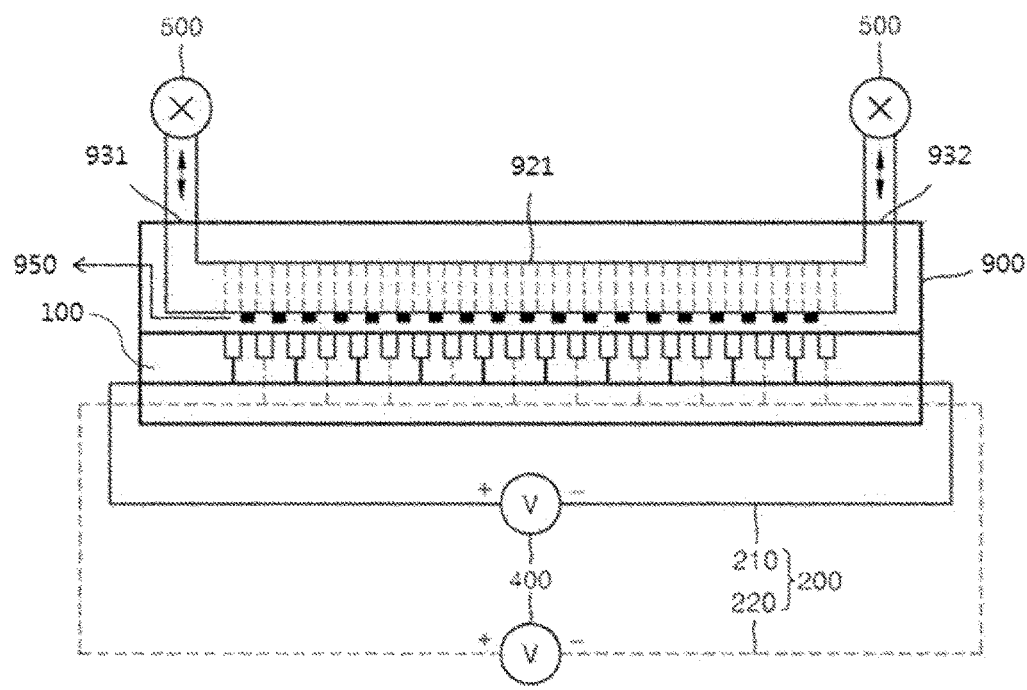
FIG. 26 depicts a PCR conducted by a PCR device having the PCR heating block 100 on which the heaters having the compensated patterns formed thereon are repeatedly arranged and the PCR reaction unit 900 of FIGS. 22 to 25.

FIG. 26 depicts a PCR conducted by a PCR device having the PCR heating block 100 on which the heaters having the compensated patterns formed thereon are repeatedly arranged and the PCR part 900 of FIGS. 22 to 25.

Referring to FIG. 26, the PCR reaction unit 900 is disposed on the PCR heating block 100, and the detection electrodes 950 are located repeatedly between the first heaters and the second heaters repeatedly arranged on the top surface of the PCR heating block 100. The PCR reaction unit 900 and the components contained therein are the same as mentioned above, and therefore, an explanation on them will be avoided for the brevity of the description.

The power supply source 400 is a module supplying power to the power supply part 200 and is connected correspondingly to the first distributed wire 210 and the second distributed wire 220 of the power supply part 200. While the PCR is being conducted, for example, a first power port (not shown) of the power supply sources 400 is electrically connected to the first distributed wire 210, and a second power port (not shown) of the power supply sources 400 is electrically connected to the second distributed wire 220. After that, if a command for conducting the PCR is issued from a user, the power supply source 400 supplies power to the first distributed wire 210 and the second distributed wire 220 and rapidly heats the first heater and the second heater of the PCR heating block 100. If the heaters reach given temperatures, further, the power supply source 400 controls the quantity of power supplied to allow the heaters to maintain the given temperatures. For example, the given temperature at each first heater is a temperature (in the range of 85 to 105° C., preferably 95° C.) of the PCR denaturing step, and the given temperature at each second heater is a temperature (in the range of 50 to 80° C., preferably 72° C.) of the PCR annealing/extension step. Otherwise, the given temperature at each first heater is a temperature (in the range of 50 to 80° C., preferably 72° C.) of the PCR annealing/extension step, and the given temperature at each second heater is a temperature (in the range of 85 to 105° C., preferably 95° C.) of the PCR denaturing step.

The pumps 500 are modules controlling the flow rate of the solution flowing in one or more reaction channels 921 of the PCR reaction unit 900, and they may provide positive pressure or negative pressure. For example, they may be syringe pumps. The pumps 500 are operably disposed on a portion of each reaction channel 921, and preferably, they are connected to the inlet 931 and/or the outlet 932 formed on both ends of each reaction channel 921. If the pumps 500 are connected to the inlet 931 and/or the outlet 932 formed on both ends of each reaction channel 921, further, they serve as stoppers preventing the sample and reagent solution from leaking through the inlet 931 and/or the outlet 932. Furthermore, if the flow rate of the fluid, that is, the sample and reagent solution flowing in each reaction channel 921 is to be controlled in one direction, the pump 500 is connected to either the inlet 931 or the outlet 932, and a general stopper is sealingly connected to the other not connected to the pump 500. Contrarily, if the flow rate of the fluid, that is, the sample and reagent solution flowing in each reaction channel 921 is to be controlled in both directions, the pumps 500 are connected to both of the inlet 931 and the outlet 932.

The nucleic acid amplification reaction of the PCR solution in the real time PCR device is conducted by the steps as follows.

At a first step, the PCR solution is prepared having desired double-stranded target DNA, oligonucleotide primer having the complimentary sequence to specific sequence to be amplified, DNA polymerase, deoxyribonucleotide triphosphates (dNTP), and PCR buffer.

At a second step, the PCR solution is introduced into the PCR reaction unit 900. In this case, the PCR solution is supplied to the reaction channels 921 of the PCR reaction unit 900 through the inlets 931.

At a third step, the power supply part 200, that is, the first distributed wire 210 and the second distributed wire 220 are connected to the power supply sources 400, and the inlets 931 and the outlets 932 of the PCR reaction unit 900 are sealingly connected to the pumps 500.

At a fourth step, power supply is commanded to the power supply source 400 to heat the first heater and the second heater through the first distributed wire 210 and the second distributed wire 220 so that the first heater maintain a given temperature (95° C.) of the PCR denaturing step, and the second heater maintain a given temperature (72° C.) of the PCR annealing/extension step.

At a fifth step, lastly, positive pressure is provided by the pumps 500 connected to the inlets 931 or negative pressure is provided by the pumps 500 connected to the outlets 932, so that the sample and reagent solution flows horizontally in the reaction channels 921. In this case, the flow rate of the sample and reagent solution is controllable by the adjustment of the positive pressure and the negative pressure provided by the pumps 500.

Through the above-mentioned steps, the PCR solution flows longitudinally along the portions corresponding to the upper side portions of the first heaters and the portions corresponding to the upper side portions of the second heaters from the ends of the inlets 931 of the reaction channels 921 to the ends of the outlets 932 thereof, thus conducting the PCR. Referring to FIG. 26, the PCR solution receives the heat from the PCR heating block 100 on which the heater units having the first heater and the second heater are repeatedly arranged 10 times and is passed through the PCR denaturing step on the portions corresponding to the upper side portions of the first heater and through the PCR annealing/extension step on the portions corresponding to the upper side portions of the second heater, thus finishing 10 PCR cycles. After that, the PCR solution reversely flows longitudinally along the portions corresponding to the upper side portions of the first heater and the portions corresponding to the upper side portions of the second heater from the ends of the outlets 932 of the reaction channels 921 to the ends of the inlets 931 thereof, thus selectively conducting the PCR again.

Figure 27:
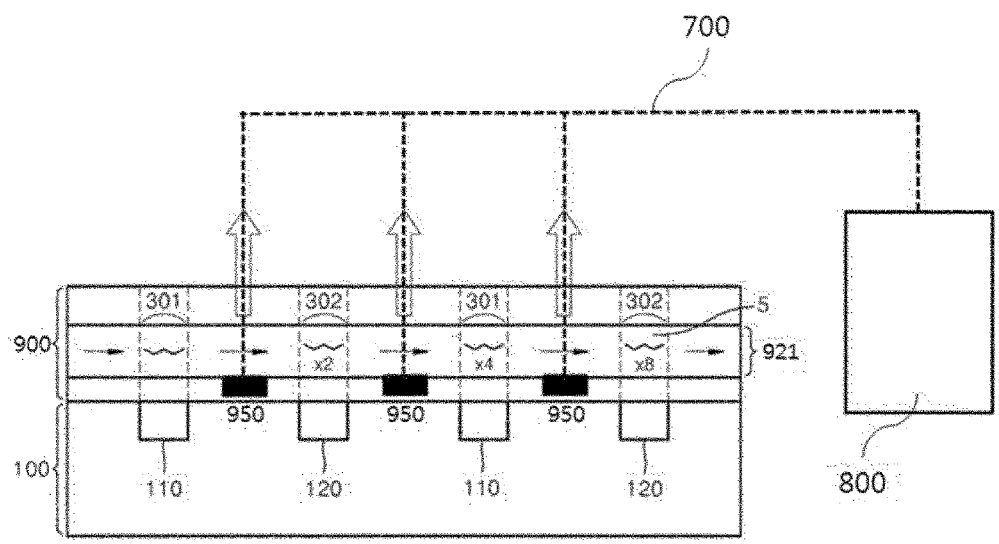
FIG. 27 depicts an electrochemical real time PCR conducted by a PCR device having the PCR heating block 100 on which the heaters having the compensated patterns formed thereon are repeatedly arranged, the PCR reaction unit 900 of FIGS. 22 to 25, the detection electrodes 950, and a signal measuring module 800.

FIG. 27 depicts an electrochemical real time PCR conducted by a PCR device having the PCR heating block 100 on which the heaters having the compensated patterns formed thereon are repeatedly arranged, the PCR part 900 of FIGS. 22 to 25, the detection electrodes 950, and a signal measuring module 800.

Referring to FIG. 27, the PCR device according to the present invention includes the PCR heating block 100 having the first heater 110 and the second heater 120 repeatedly arranged in a horizontal direction thereof, the PCR reaction unit 900 having the detection electrodes 950 repeatedly arranged in the space between the first heater 110 and the second heater 120, and a signal measuring module 800 electrically connected to a connection port (not shown) of a chip holder (not shown) to in real time measure the electrochemical signals generated from the interiors of the reaction channels 921 of the PCR reaction unit 900. Even if not shown, the PCR device further includes a power supply part and pumps. The electrochemical signal measuring module 800 is electrically connected to the connection port of the chip holder by electrical connection means 700 like lead wire. Accordingly, the electrochemical signals repeatedly generated through the successive nucleic acid amplification from the interiors of the reaction channels 921 of the PCR reaction unit 900 are sequentially detected through the detection electrodes 950 of the PCR reaction unit 900, and the detected signals are measured and further processed or analyzed in the electrochemical signal measuring module 800 through the connection port of the chip holder and the electrical connection means 700. The electrochemical signal measuring module 800 is provided in various manners, and preferably, it is selected from the group consisting of anodic stripping voltammetry (ASV), chronoamperometry (CA), cyclic voltammetry, square wave voltammetry (SWV), differential pulse voltammetry (DPV), and impedance. Accordingly, the real time PCR device can measure and analyze the nucleic acid amplification in real time during the PCR. Unlike the optical real time PCR device, in this case, there is no need to add a fluorescent material to the PCR solution. Accordingly, the nucleic acid amplification reaction can be monitored in real time through the real time PCR device. For example, the PCR solution is successively passed through portions 301 corresponding to the upper side portions of the first heater 110 and portions 302 corresponding to the upper side portions of the second heaters 120 in the reaction channels 921, thus conducting the PCR denaturing step and the PCR annealing/extension step. In this case, the PCR solution is passed through the portions corresponding to the detection electrodes 950 repeatedly arranged between the first heater 110 and the second heater 120 and between the heater units each having the first heater 110 and the second heater 120. When the PCR solution is passed through the portions corresponding to the upper sides of the detection electrodes 950, the PCR solution flows slowly or momentarily stops through control, and at this time, the electrochemical signals generated by the bonding of the amplified nucleic acid to the redox indicator are successively detected in real time and measured through the detection electrodes 950. During the PCR cycles, accordingly, the reaction results of the nucleic acid amplification in the reaction channels 921 (having no fluorescent material and light detection system) are monitored in real time, thus allowing the quantity of target DNA to be measured and analyzed in real time.

FIGS. 28 to 31 depicts another type of a PCR part 900 having thermal contact with the PCR heating block of FIGS. 12 to 16.

A PCR reaction unit 900 as shown in FIGS. 28 to 31 includes immobilization layers 940 repeatedly spaced apart from each other on one region of the interiors of the reaction channels 921 in such a manner as to traverse the sections of the reaction channels 921 in longitudinal directions of the reaction channels 921 and subjected to surface treatment with capture probes complementarily bonded to one region of the amplified target nucleic acid, and detection electrodes 950 formed on the other region of the reaction channels 921 so as to detect the electrochemical signals. The reaction channels 921 contain composites having metal nanoparticles and signaling probes connected to the metal nanoparticles in such a manner as to be complementarily bonded to the other region of the amplified target nucleic acid.

The PCR reaction unit 900 is disposed on top of the PCR heating block 100 and includes the reaction channels 921 each having the inlet 931 and the outlet 932 formed on both ends thereof, the immobilization layers 940 repeatedly spaced apart from each other on one region of the interiors of the reaction channels 921 in such a manner as to traverse the sections of the reaction channels 921 in the longitudinal directions of the reaction channels 921 and subjected to surface treatment with the capture probes complementarily bonded to one region of the amplified target nucleic acid, and the detection electrodes 950 formed on the other region of the reaction channels 921 so as to detect the electrochemical signals.

Figure 29:
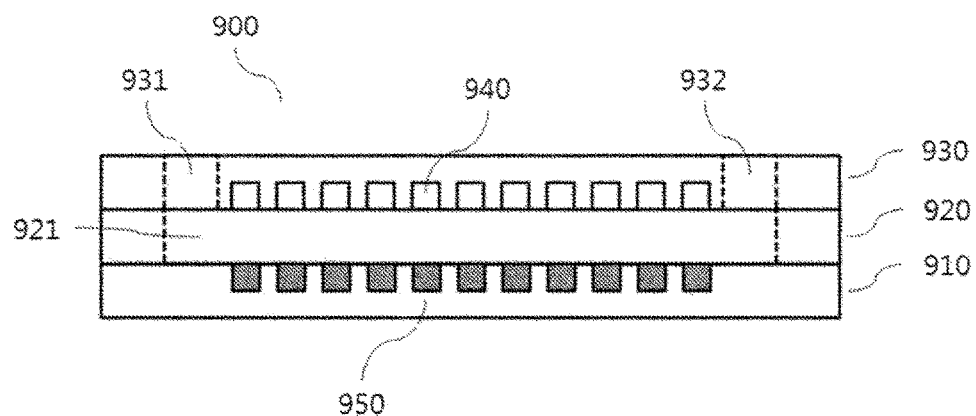

The reaction channels 921 are spaces in which the PCR is conducted by the PCR solution and have various shapes and structures like hollow cylinders, bars, and rectangular pillars. On one region of the reaction channels 921, further, the immobilization layers 940 are subjected to surface treatment with the capture probes complementarily bonded to one region of the amplified target nucleic acid, and on the other region of the reaction channels 921, the detection electrodes 950 are formed to detect the electrochemical signals. The immobilization layers 940 and the detection electrodes 950 are located at various positions, and as shown in FIG. 29, preferably, they face each other in up and down directions or in left and right directions. Further, the reaction channels 921 contain the composites accommodated thereinto, and the composites include the metal nanoparticles and the signaling probes connected to the metal nanoparticles and complementarily bonded to the other region of the amplified target nucleic acid. In this case, the composites are previously contained in the reaction channels 921 before the PCR sample containing the template nucleic acid is introduced, and otherwise, they are introduced into the reaction channels 921 in the state of being contained in the PCR reagents like the primer and the polymerase. The immobilization layers 940 are made of various materials like silicone, plastic, glass and metal materials so that the capture probes are deposited and exposed on one surface thereof. Before the deposition of the capture probes, the surfaces of the immobilization layers 940 are first subjected to surface treatment with a material like amine group ($-NH_3^+$), aldehyde group ($-COH$), and carboxyl group ($-COOH$). The capture probes are complementarily bonded to one portion (region) of the amplified target nucleic acid and form the composites through the bonding to the metal nanoparticles. The metal nanoparticles are made of various metals, and preferably, they are made of one or more materials selected from the group consisting of Zn, Cd, Pb, Cu, Ga, In, Au, Cr, Mn, Fe, Co, Ni, Cs, Ba, Cd, Hg, As, Se, Sn, Sb, Bi and Ag. The signaling probes are complementarily bonded to one region of the amplified target nucleic acid, and in this case, the complementarily bonded region of the amplified target nucleic acid to the signaling probes is different from that to the capture probes. Accordingly, the capture probes and the signaling probes can be complementarily bonded to the amplified target nucleic acid. If the target DNA is amplified in the reaction channels 921 during the PCR, that is, the amplified target nucleic acid is complementarily bonded to the capture probes treated on the surfaces of the immobilization layers 940 and further complementarily bonded to the signaling probes connected to the metal nanoparticles, thus allowing the metal nanoparticles to be collected to the regions adjacent to the immobilization layers 940. As a result, the metal nanoparticles do not reach the detection electrodes 950, thus causing the current variations (reduction) between the metal nanoparticles and the detection electrodes 950 and generating detectable electrochemical signals according to the amplification of the target DNA. On the other hand, the amplified target nucleic acid, the capture probes and the signaling probes are formed of single-stranded DNA.

Figure 28:
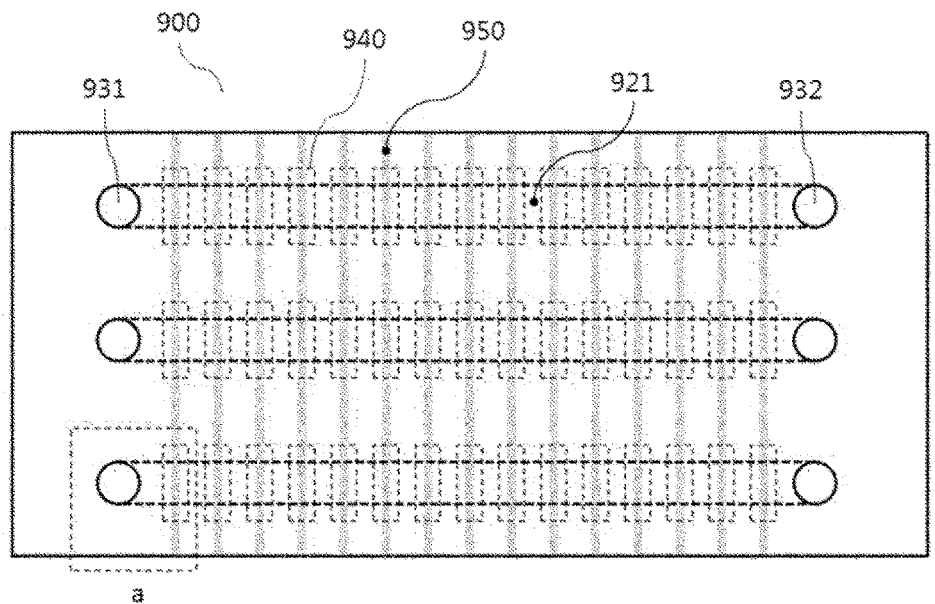
FIGS. 28 to 31 depicts another type of a PCR reaction unit 900 having thermal contact with the PCR heating block of FIGS. 12 to 16.

The detection electrodes 950 are disposed on at least one region of the reaction channels 921 to detect the electrochemical signals generated in the interiors of the reaction channels 921. So as to conduct the detection, the detection electrodes 950 are made of various materials, and for example, they are made of one or more materials selected from the group consisting of Au, Co, Pt, Ag, carbon nanotube, graphene, and carbon. Further, the detection electrodes 950 have various shapes and structures capable of effectively detecting the electrochemical signals generated in the interiors of the reaction channels 921, and for example, as shown in FIG. 28, they have a shape of a plate made of a metal material disposed along the inner surfaces of the reaction channels 921. On the other hand, the electrochemical signals are measured by an electrochemical signal measuring module as will be discussed later, and the electrochemical signal measuring module is provided in various manners. Preferably, the electrochemical signal measuring module is selected from the group consisting of anodic stripping voltammetry (ASV), chronoamperometry (CA), cyclic voltammetry, square wave voltammetry (SWV), differential pulse voltammetry (DPV), and impedance. The electrochemical signals are generated from the current variations caused by the complementary bonding of the amplified target nucleic acid to the capture probes and the signaling probes. The process in which the electrochemical signals are generated in the PCR device according to the present invention is as follows. At a first step, before the PCR starts, the capture probes treated on the surfaces of the immobilization layers and the composites (signaling probes-metal nanoparticles) including the signaling probes and the metal nanoparticles are in their original state, at a second step, current variations (signals) are generated from the reduction or oxidation between the working electrodes and the metal nanoparticles, and at a third step, after the PCR has started, the amplified target nucleic acid is bonded to the capture probes and the signaling probes of the composites to cause the reduction of the current variations (signals). In more detail, if the reduction voltage is applied to the metal nanoparticles of the composites, the metal nanoparticles are collected to the surfaces adjacent to the working electrodes and thus form accumulation layers while being reduced. Then, if a voltage is applied to the working electrodes, the reduced metal nanoparticles are oxidized (stripped) to generate the current variations (signals), and the current variations are easily measured through the voltage values indicated by the oxidation current peaks. In this case, the current variation values, that is, the electrochemical signals generated in the interiors of the reaction channels 921 indicate the quantity of variations of the target DNA. Also, the voltage values at which the metal nanoparticles are oxidized are different in accordance with the kinds of the metal nanoparticles, and in case of two kinds of metal nanoparticles, accordingly, the signals for two or more samples can be detected at the same time. After that, if the PCR is conducted, the target DNA is amplified from the template DNA, and the amplified target nucleic acid is complementarily bonded (hybridized target DNA) to the capture probes and the signal probes of the composites (signaling probes-metal nanoparticles), thus inhibiting the accumulation of the metal nanoparticles of the composites and decreasing the current values. As the PCR cycles are increased, further, the quantity of the amplified target nucleic acid is increased to allow the complementarily bonding (hybridized target DNA) to the capture probes and the signal probes of the composites to be raised, thus more decreasing the current values. Accordingly, the reduction of the current variations, that is, the electrochemical signals is detected and measured, thus conducting the PCR in real time.

Referring to FIGS. 28 and 29, the immobilization layers 940 and the detection electrodes 950 are repeatedly spaced apart from each other in such a manner as to traverse the sections of the reaction channels 921 in longitudinal directions of the reaction channels 921, and when come into thermal contact with the PCR heating block 100, they are located between the two heater groups 110, 120 and 130. Referring to FIG. 28 illustrating the plan of the PCR reaction unit 900, the immobilization layers 940 and the detection electrodes 950 are repeatedly spaced apart from each other on the regions of the reaction channels 921 from the inlets 931 and the outlets 932 in such a manner as to pass through the reaction channels 921 in longitudinal directions of the reaction channels 921, thus repeatedly detecting the electrochemical signals from the successively amplified DNA. Referring to FIG. 29 illustrating the vertical section of the PCR reaction unit 900, the immobilization layers 940 and the detection electrodes 950 face each other on the sections of the reaction channels 921, and in this case, their position may be changed in up and down directions.

Referring to FIG. 29, the PCR reaction unit 900 is divided largely into three layers with respect to the vertical section thereof. The PCR reaction unit 900 includes a first plate 910 on which the detection electrodes 950 are disposed, a second plate 920 disposed on top of the first plate 910 and having one or more reaction channels 921, and a third plate 930 disposed on top of the second plate 920 and having the immobilization layers 940, the inlets 931 and the outlets 932 formed thereon. In this case, of course, the detection electrodes 950 may be disposed on the third plate 930, and the immobilization layers 940 may be formed on the first plate 910.

The top surface of the first plate 910 on which the detection electrodes 950 are disposed is bonded to the underside surface of the second plate 920. The first plate 910 is bonded to the second plate 920 having the reaction channels 921, thus ensuring the space for the reaction channels 921 and further allowing the detection electrodes 950 to be disposed on at least one region (surface) of the reaction channels 921. On the other hand, the first plate 910 is made of various materials, and preferably, it is made of a material selected from the group consisting of polydimethylsiloxane (PDMS), cyclo-olefin copolymer (COC), polymethylmetharcylate (PMMA), polycarbonate (PC), polypropylene carbonate (PPC), polyether sulfone (PES), polyethylene terephthalate (PET), and a combination thereof. Further, a hydrophilic substance (not shown) is applied to the top surface of the first plate 910 so as to serve to gently conduct the PCR. Through the application of the hydrophilic substance, accordingly, a single layer containing the hydrophilic substance is formed on the first plate 910. The hydrophilic substance includes various materials, and preferably, it includes a material selected from the group consisting of carboxyl group (—COOH), amine group (—NH2), hydroxyl group (—OH), and sulfone group (—SH). The application of the hydrophilic substance is conducted in a manner known in the art.

The top surface of the second plate 920 is bonded to the underside surface of the third plate 930. The second plate 920 includes the reaction channels 921. The reaction channels 921 are connected to the inlets 931 and the outlets 932 formed on the third plate 930, thus allowing the inlets 931 and the outlets 932 to be formed on both ends thereof. Accordingly, a PCR sample and reagent is introduced into the reaction channels 921, and next, the PCR is conducted. Further, two or more reaction channels 921 may be formed in accordance with the use purposes and ranges of the PCR device according to the present invention. The second plate 920 is made of various materials, and preferably, it is made of a thermoplastic resin or thermosetting resin selected from the group consisting of polymethylmetharcylate (PMMA), polycarbonate (PC), cyclo-olefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoralkoxyalkane (PFA), and a combination thereof. Further, the second plate 920 has various thicknesses, and preferably, it has a thickness of 100 to 200 μm. The reaction channels 921 have various widths and lengths, and preferably, have a width of 0.001 mm to 10 mm and a length of 1 mm to 400 mm. Furthermore, the inner wall of the second plate 920 is coated with a material like silane group, bovine serum albumin (BSA) and so on to prevent DNA and protein from being absorbed thereto. The application of the material is conducted in a manner known in the art.

The underside surface of the third plate 930 is disposed on top of the second plate 920. The third plate 930 has the immobilization layers 940, the inlets 931 and the outlets 932 formed on the reaction channels 921. The inlets 931 are portions into which the PCR sample and reagents are introduced. The outlets 932 are portions through which the PCR products after the completion of the PCR are discharged. Accordingly, the third plate 930 covers the reaction channels 921 formed on the second plate 920, while allowing the inlets 931 and the outlets 932 to serve as the inlets and outlets of the reaction channels 921. Further, the third plate 930 is made of various materials, and preferably, it is made of a material selected from the group consisting of polydimethylsiloxane (PDMS), cyclo-olefin copolymer (COC), polymethylmetharcylate (PMMA), polycarbonate (PC), polypropylene carbonate (PPC), polyether sulfone (PES), polyethylene terephthalate (PET), and a combination thereof. Further, the inlets 931 have various sizes, and preferably, they have a diameter of 1.0 to 3.0 mm. Furthermore, the outlets 932 have various sizes, and preferably, they have a diameter of 1.0 to 1.5 mm. In addition, cover means (not shown) are mounted on the inlets 931 and the outlets 932 so as to prevent the PCR sample and reagents from leaking when the PCR for the PCR sample and reagents is conducted on the reaction channels 921. The cover means have various shapes, sizes or materials. Further, the third plate 930 has various thicknesses, and preferably, it has a thickness of 0.1 to 2.0 mm. On the other hand, two or more inlets 931 and outlets 932 may be formed on the third plate 930.

On the other hand, the PCR reaction unit 900 is easily made through a method including the steps of: providing the third plate 930 having the inlets 931 and the outlets 932 formed by machining, forming the reaction channels 921 by machining over portions corresponding to the inlets 931 and the outlets 932 of the third plate 930 on a plate having the corresponding size to the underside surface of the third plate 930 to provide the second plate 920, forming a surface containing the hydrophilic substance by surface treatment on the top surface of a plate having the corresponding size to the underside surface of the second plate 920 to provide the first plate 910, and bonding the underside surface of the third plate 930 to the top surface of the second plate 920 and bonding the underside surface of the second plate 920 to the top surface of the first plate 910. The inlets 931 and the outlets 932 of the third plate 930 and the reaction channels 921 of the second plate 920 are formed by a machining method selected from the group consisting of injection molding, hot-embossing, casting, and laser ablation. Further, the hydrophilic substance on the surface of the first plate 910 is applied thereto by a method selected from the group consisting of oxygen and argon plasma treatment, corona discharge, and surface active agent coating, and the application of the hydrophilic substance is conducted in a manner known in the art. Also, the bonding of the underside surface of the third plate 930 to the top surface of the second plate 920 and the bonding of the underside surface of the second plate 920 to the top surface of the first plate 910 are conducted by thermal bonding, ultrasonic welding, solvent bonding, hot plate welding, ultraviolet bonding, and press bonding in a manner known in the art. Further, a double-sided adhesive, a thermoplastic resin or a thermosetting resin (which is not shown) may be applied to the spaces between the third plate 930 and the second plate 920 and between the second plate 920 and the first plate 910.

Figure 30:
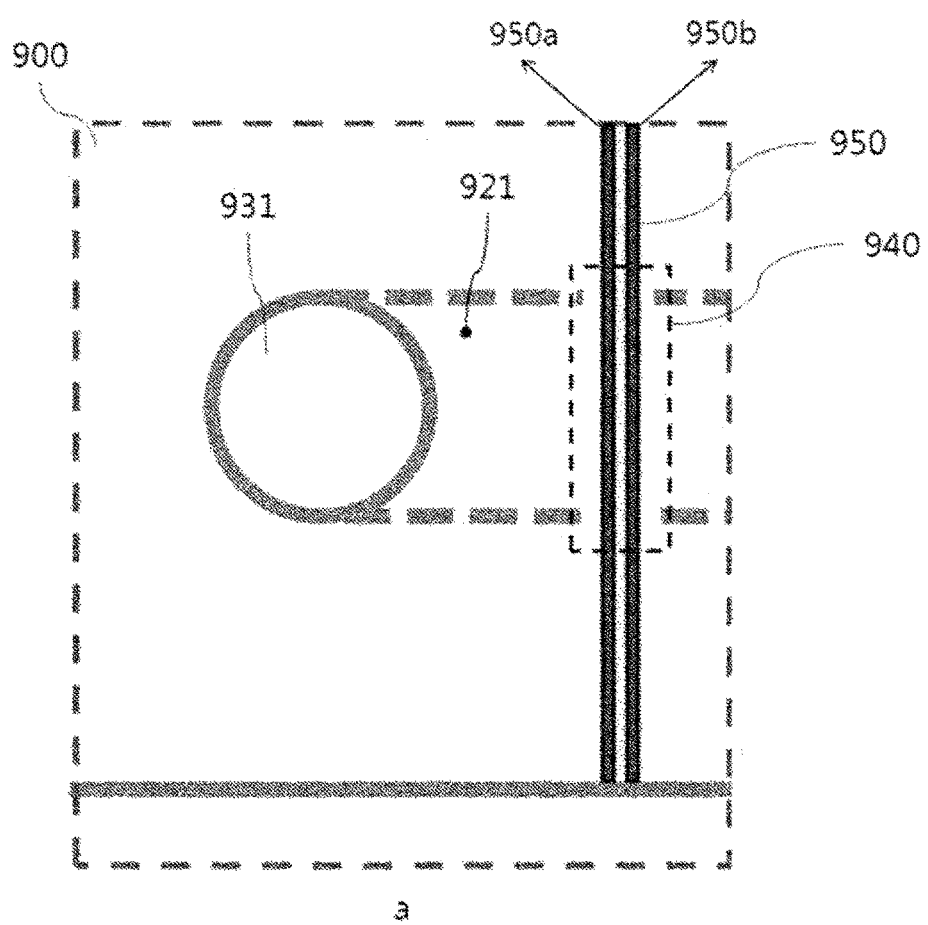
Figure 31:
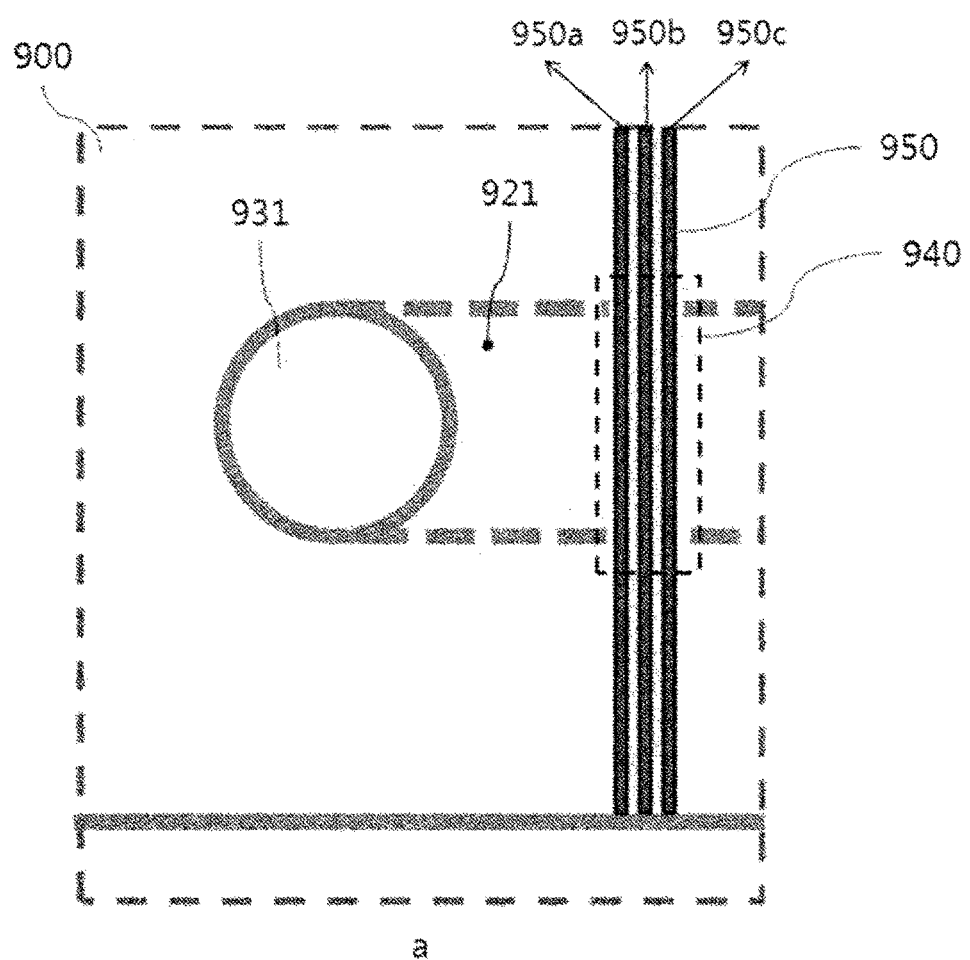

Referring to FIGS. 30 and 31 illustrating an enlarged portion "a" of FIG. 28, on the other hand, the detection electrodes 950 are provided in various manners. Referring to FIG. 30, for example, each detection electrode 950 is formed of a two-electrode module including a working electrode 950a on which oxidation or reduction reaction occurs and a reference electrode 950b on which oxidation or reduction reaction does not occur. Referring to FIG. 31, for example, each detection electrode 950 is formed of a three-electrode module including the working electrode 950a, the reference electrode 950b, and a counter electrode 950c for adjusting the balance of electrodes generated from the working electrode 950a. If the detection electrode 950 is configured as a multiple electrode module, like this, the sensitivity of the electrochemical signals generated in the reaction channels 921 can be enhanced, and further, the detection and measurement of the generated signals can be easily conducted.

Figure 32:
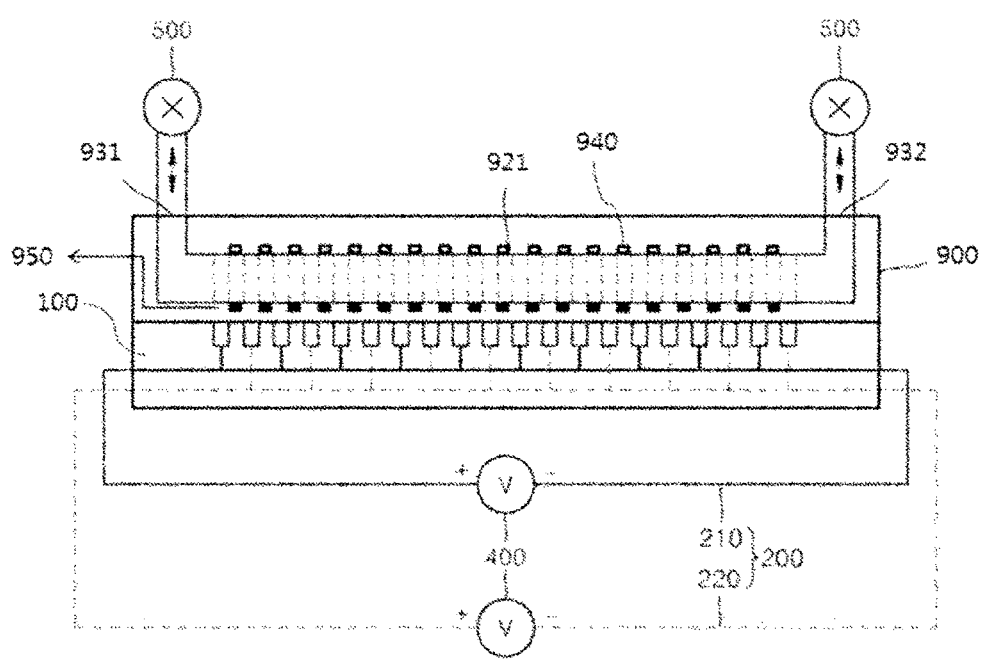
FIG. 32 depicts PCR conducted by the PCR device having the PCR heating block 100 on which the heaters having the compensated patterns formed thereon are repeatedly arranged and the PCR reaction unit 900 of FIGS. 28 to 31.

FIG. 32 depicts PCR conducted by the PCR device having the PCR heating block 100 on which the heaters having the compensated patterns formed thereon are repeatedly arranged and the PCR part 900 of FIGS. 28 to 31.

Referring to FIG. 32, the PCR reaction unit 900 is disposed on the PCR heating block 100, and in more detail, the detection electrodes 950 are repeatedly disposed between the first heater and the second heater repeatedly arranged on the top surface of the PCR heating block 100. The power supply sources 400 are modules supplying power to the power supply part 200 and connected correspondingly to the first distributed wire 210 and the second distributed wire 220 of the power supply part 200. While the PCR is being conducted, for example, a first power port (not shown) of the power supply sources 400 is electrically connected to the first distributed wire 210, and a second power port (not shown) of the power supply sources 400 is electrically connected to the second distributed wire 220. After that, if a command for conducting the PCR is issued from a user, the power supply sources 400 supply power to the first distributed wire 210 and the second distributed wire 220 and rapidly heats the first heaters and the second heaters of the PCR heating block. If the heaters reach given temperatures, further, the power supply sources 400 control the quantity of power supplied to allow the heaters to maintain the given temperatures. For example, the given temperature at each first heater 110 is a temperature of the PCR denaturing step (in the range of 85 to 105° C., preferably 95° C.), and the given temperature at each second heater is a temperature of the PCR annealing/extension step (in the range of 50 to 80° C., preferably 72° C.). Otherwise, the given temperature at each first heater is a temperature of the PCR annealing/extension step (in the range of 50 to 80° C., preferably 72° C.), and the given temperature at each second heater is a temperature of the PCR denaturing step (in the range of 85 to 105° C., preferably 95° C.).

The pumps 500 are modules controlling the flow rate of the solution flowing in one or more reaction channels 921 of the PCR reaction unit 900, and they may provide positive pressure or negative pressure. For example, they may be syringe pumps. The pumps 500 are operably disposed on a portion of each reaction channel 921, and preferably, they are connected to the inlet 931 and/or the outlet 932 formed on both ends of each reaction channel 921. If the pumps 500 are connected to the inlet 931 and/or the outlet 932 formed on both ends of each reaction channel 921, further, they serve as stoppers preventing the sample and reagent solution from leaking through the inlet 931 and/or the outlet 932. Furthermore, if the flow rate of the fluid, that is, the sample and reagent solution flowing in each reaction channel 921 is to be controlled in one direction, the pump 500 is connected to either the inlet 931 or the outlet 932, and a general stopper has a sealing connection to the other not connected to the pump 500. Contrarily, if the flow rate of the fluid, that is, the sample and reagent solution flowing in each reaction channel 921 is to be controlled in both directions, the pumps 500 are connected to both of the inlet 931 and the outlet 932.

The nucleic acid amplification reaction of the PCR solution in the real time PCR device is conducted by the steps as follows.

At a first step, the PCR solution is prepared having desired double-stranded target DNA, oligonucleotide primer having the complimentary sequence to specific sequence to be amplified, DNA polymerase, deoxyribonucleotide triphosphates (dNTP), and PCR buffer.

At a second step, the PCR solution is introduced into the PCR reaction unit 900. In this case, the PCR solution is supplied to the reaction channels 921 of the PCR reaction unit 900 through the inlets 931.

At a third step, the power supply part 200, that is, the first distributed wire 210 and the second distributed wire 220 are connected to the power supply sources 400, and the inlets 931 and the outlets 932 of the PCR reaction unit 900 has a sealing connection to the pumps 500.

At a fourth step, power supply is commanded to the power supply sources 400 to heat the first heaters 110 and the second heaters 120 through the first distributed wire 210 and the second distributed wire 220 so that the first heaters maintain the given temperature (95° C.) of the PCR denaturing step, and the second heaters maintain the given temperature (72° C.) of the PCR annealing/extension step.

At a fifth step, lastly, the positive pressure is provided by the pumps 500 connected to the inlets 931 or the negative pressure is provided by the pumps 500 connected to the outlets 932, so that the sample and reagent solution flows horizontally in the reaction channels 921. In this case, the flow rate of the sample and reagent solution is controllable by the adjustment of the positive pressure and the negative pressure provided by the pumps 500.

Through the above-mentioned steps, the PCR solution flows longitudinally along the portions corresponding to the upper side portions of the first heaters and the portions corresponding to the upper side portions of the second heaters from the ends of the inlets 931 of the reaction channels 921 to the ends of the outlets 932 thereof, thus conducting the PCR. The PCR solution receives the heat from the PCR heating block 100 on which the heater units having the first heaters 110 and the second heaters 120 are repeatedly arranged 10 times and is passed through the PCR denaturing step on the portions corresponding to the upper side portions of the first heaters 110 and through the PCR annealing/extension step on the portions corresponding to the upper side portions of the second heaters 120, thus finishing 10 times PCR cycles. After that, the PCR solution reversely flows longitudinally along the portions corresponding to the upper side portions of the first heaters 110 and the portions corresponding to the upper side portions of the second heaters 120 from the ends of the outlets 932 of the reaction channels 921 to the ends of the inlets 931 thereof, thus selectively conducting the PCR again.

Figure 33:
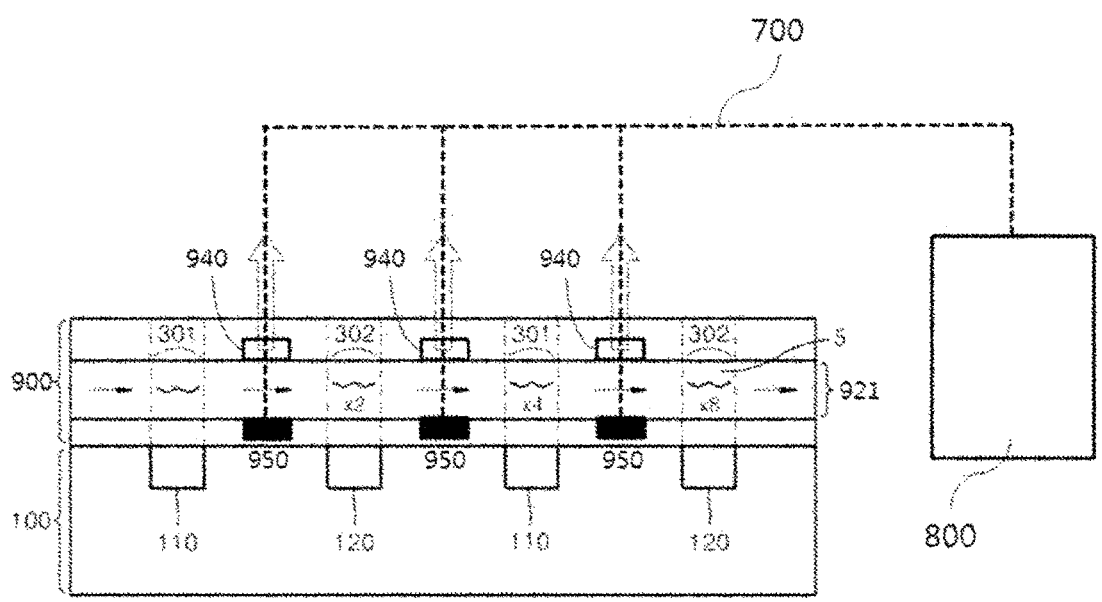
FIG. 33 depicts an electrochemical real time PCR conducted by a PCR device having the PCR heating block 100 on which the heaters having the compensated patterns formed thereon are repeatedly arranged, the PCR reaction unit 900 of FIGS. 28 to 31, the immobilization layers 940 and the detection electrodes 950, and a signal measuring module 800.

FIG. 33 depicts an electrochemical real time PCR conducted by a PCR device having the PCR heating block 100 on which the heaters having the compensated patterns formed thereon are repeatedly arranged, the PCR part 900 of FIGS. 28 to 31, the immobilization layers 940 and the detection electrodes 950, and a signal measuring module 800.

Referring to FIG. 33, the PCR device according to the present invention includes the PCR heating block 100 having the first heaters 110 and the second heaters 120 repeatedly arranged in a horizontal direction thereof, the PCR reaction unit 900 having the immobilization layers 940 and the detection electrodes 950 repeatedly arranged facingly in the spaces between the first heaters 110 and the second heaters 120, and a signal measuring module 800 electrically connected to a connection port (not shown) of a chip holder (not shown) to in real time measure the electrochemical signals generated from the interior of the reaction channels 921 of the PCR reaction unit 900. Even if not shown, the PCR device further includes a power supply part and pumps. The electrochemical signal measuring module 800 is electrically connected to the connection port of the chip holder by electrical connection means 700 like lead wire. Accordingly, the electrochemical signals repeatedly generated through the successive nucleic acid amplification from the interiors of the reaction channels 921 of the PCR reaction unit 900 are sequentially detected through the detection electrodes 950 of the PCR reaction unit 900, and the detected signals are measured and further processed or analyzed in the electrochemical signal measuring module 800 through the connection port of the chip holder and the electrical connection means 700. The electrochemical signal measuring module 800 is provided in various manners, and preferably, it is selected from the group consisting of anodic stripping voltammetry (ASV), chronoamperometry (CA), cyclic voltammetry, square wave voltammetry (SWV), differential pulse voltammetry (DPV), and impedance. Accordingly, the real time PCR device as shown in FIG. 33 can measure and analyze the nucleic acid amplification in real time during the PCR. Unlike the conventional real time PCR device, in this case, there is no need to add a fluorescent material to the PCR solution. Accordingly, the nucleic acid amplification reaction can be in real time monitored through the real time PCR device. For example, the PCR solution is successively passed through portions 301 corresponding to the upper side portions of the first heaters 110 and portions 302 corresponding to the upper side portions of the second heaters 120 in the reaction channels 921, thus conducting the PCR denaturing step and the PCR annealing/extension step. In this case, the PCR solution is passed through the portions corresponding to the detection electrodes 950 repeatedly arranged between the first heaters 110 and the second heaters 120 and between the heater units each having the first heater 110 and the second heater 120. When the PCR solution is passed through the portions corresponding to the upper sides of the detection electrodes 950, the PCR solution flows slowly or momentarily stops through control, and at this time, the electrochemical signals (current variations) generated by the bonding of the amplified target nucleic acid to the capture probes and the signaling probes of the composites are successively and in real time detected and measured through the detection electrodes 950. During the PCR cycles, accordingly, the reaction results of the nucleic acid amplification in the reaction channels 921 (having no fluorescent material and light detection system) are monitored in real time, thus allowing the quantity of target DNA to be measured and analyzed in real time.

The invention claimed is:

1. A PCR heating block comprising heaters repeatedly arranged thereon,
   wherein a pattern is disposed on a surface of each of the heaters and adjusts a resistance of the each of the heaters by spaces repeatedly disposed on at least a portion of the each of the heaters, and
   wherein the pattern controls heating uniformity on the surface of the each of the heaters.

2. The PCR heating block of claim 1, wherein the resistance has a repeated pattern of the spaces which control the heat uniformity on the surface of each of the heaters.

3. The PCR heating block of claim 2, wherein the repeated pattern of the spaces has a plurality of line widths, and wherein a part of the plurality of line widths have a different length from a remainder of the plurality of line widths and controls the heat uniformity on the surface of each of the heaters.

4. The PCR heating block of claim 1, wherein at least a portion of the resistance has a different thickness from a remainder thereof to control the heat uniformity on the surface of each of the heaters.

5. The PCR heating block of claim 1, wherein at least a portion resistance is comprised of a different material from a remainder thereof to control the heat uniformity on the surface of the each of the heaters.

6. The PCR heating block of claim 1, wherein at least a portion resistance has a different arrangement from a remainder thereof to control the heat uniformity on the surface of each of the heaters.

7. A PCR chip comprising:
   a PCR heating block comprising heaters repeatedly arranged thereon,
   wherein a pattern is disposed on a surface of each of the heaters and adjusts a resistance of the each of the heaters by spaces repeatedly disposed on at least a portion of the each of the heaters, wherein the pattern controls heating uniformity on the surface of each of the heaters and wherein the each of the heaters is extended in a first direction; and
   a PCR reaction assembly disposed on the PCR heating block, wherein the PCR heating block is configured to perform heat exchange with the PCR reaction assembly,
   wherein the PCR reaction assembly has at least one reaction channel extended in a second direction, and each of the at least one reaction channel has an inlet and an outlet defined on both ends thereof, and
   wherein the first direction is different from the second direction.

8. The PCR chip of claim 7, wherein an insulator is interposed between the PCR heating block and the PCR reaction assembly.

9. The PCR chip of claim 7, wherein the first direction is normal to the second direction.

10. A PCR device comprising:
    a PCR heating block comprising heaters repeatedly arranged thereon,
    wherein a pattern is disposed on a surface of of the heaters and adjusts a resistance of the each of the heaters by spaces repeatedly disposed on at least a portion of the each of the heaters,
    wherein the pattern controls heating uniformity on the surface of the each of the heaters, and wherein each of the heaters is extended in a first direction; and
    a PCR reaction assembly detachably attached or fixedly attached to the PCR heating block, wherein the PCR heating block is configured to perform heat exchange with the PCR reaction assembly,
    wherein the PCR reaction assembly has at least one reaction channel extended in a second direction, and each of the at least one reaction channel has an inlet and an outlet defined on both ends thereof, and
    wherein the first direction is different from the second direction; and
    a power supply assembly supplying power to the heaters.

11. The PCR device of claim 10, wherein an insulator is disposed on the PCR heating block and is disposed to face the PCR reaction assembly.

12. The PCR device of claim 10, further comprising a pump configured to provide positive pressure or negative pressure to a PCR solution in the at least one reaction channel to control a rate of flow and a velocity of flow thereof.

13. The PCR device of claim 10, further comprising:
    a light source configured to provide light to the PCR reaction assembly; and
    a light detector configured to detect the light emitted from the light source.

14. The PCR device of claim 13, wherein the light source and the light detector are disposed in-between two adjacent heaters of the heaters.

15. The PCR device of claim 10, wherein the PCR reaction assembly comprises a plurality of detection electrodes spaced apart from one another, extended in the second direction, and disposed in-between the at least one reaction channel and the heaters,
    wherein each of the plurality of detection electrodes is disposed to face a space defined by two adjacent heaters of the heaters, and
    wherein the plurality of detection electrodes is configured to detect electrochemical signals generated from bonding of amplified nucleic acid and a redox indicator in the at least one reaction channel.

16. The PCR device of claim 15, further comprising an electrochemical signal measuring module electrically coupled to the plurality of detection electrodes for real time measurement of the electrochemical signals.

17. The PCR device of claim 10, wherein the PCR reaction assembly comprises a plurality of immobilization layers spaced apart from one another, extended in the second direction, and having capture probes complementarily bonded to one region of amplified target DNA,
    wherein the at least one reaction channel is interposed between the plurality of immobilization layers and the plurality of detection electrodes,
    wherein the at least one reaction channel is configured to contain composites which have metal nanoparticles and signaling probes, and
    wherein the signaling probes are configured to connect to the metal nanoparticles and complementarily bond to the other region of the amplified target DNA.

18. The PCR device of claim 17, further comprising an electrochemical signal measuring module electrically coupled to the plurality of detection electrodes for real time measurement of the electrochemical signals.

19. The PCR chip of claim 10, wherein the first direction is normal to the second direction.

* * * * *